United States Patent [19]
Brown

[11] Patent Number: 5,997,476
[45] Date of Patent: Dec. 7, 1999

[54] NETWORKED SYSTEM FOR INTERACTIVE COMMUNICATION AND REMOTE MONITORING OF INDIVIDUALS

[75] Inventor: Stephen J. Brown, Mountain View, Calif.

[73] Assignee: Health Hero Network, Inc., Mountain View, Calif.

[21] Appl. No.: 08/946,341

[22] Filed: Oct. 7, 1997

Related U.S. Application Data

[63] Continuation of application No. 08/847,009, Apr. 30, 1997, Pat. No. 5,897,493
[60] Provisional application No. 60/041,746, Mar. 28, 1997, and provisional application No. 60/041,751, Mar. 28, 1997.

[51] Int. Cl.⁶ ..................................................... A61N 5/00
[52] U.S. Cl. .......................... 600/300; 600/301; 128/920; 705/2; 705/3
[58] Field of Search .................................... 600/300, 301; 379/93; 705/2, 3; 128/904, 905, 920–925, 897–898

[56] References Cited

U.S. PATENT DOCUMENTS

| | | | |
|---|---|---|---|
| 5,299,121 | 3/1994 | Brill et al. | 600/301 |
| 5,390,238 | 2/1995 | Kirk et al. | 379/93 |
| 5,410,471 | 4/1995 | Alyfuku et al. | 600/300 |
| 5,434,611 | 7/1995 | Tamura | 348/8 |
| 5,441,047 | 8/1995 | David et al. | 128/670 |
| 5,544,649 | 8/1996 | David et al. | 600/301 |
| 5,619,991 | 4/1997 | Sloane | 600/300 |

FOREIGN PATENT DOCUMENTS

| | | | |
|---|---|---|---|
| 0251520 | 1/1988 | European Pat. Off. | 15/42 |
| 0320749 | 6/1989 | European Pat. Off. | 15/42 |
| 9520199 | 7/1995 | WIPO . | |
| 9708605 | 3/1997 | WIPO . | |

*Primary Examiner*—Cary O'Connor
*Assistant Examiner*—Michael Astorino
*Attorney, Agent, or Firm*—Lumen Intellectual Property Services

[57] ABSTRACT

The invention presents a networked system for communicating information to an individual and for remotely monitoring the individual. The system includes a server and a remote interface for entering in the server a set of queries to be answered by the individual. The server is preferably a web server and the remote interface is preferably a personal computer or remote terminal connected to the server via the Internet. The system also includes a remotely programmable apparatus connected to the server via a communication network, preferably the Internet. The apparatus interacts with the individual in accordance with a script program received from the server. The server includes a script generator for generating the script program from the set of queries entered through the remote interface. The script program is received and executed by the apparatus to communicate the queries to the individual, to receive responses to the queries, and to transmit the responses from the apparatus to the server.

50 Claims, 15 Drawing Sheets

SCRIPT ENTRY SCREEN

SCRIPT NAME: DIABETES SCRIPT 1

| QUERIES | CHOICE 1 | CHOICE 2 | CHOICE 3 | CHOICE 4 |
|---|---|---|---|---|
| HOW DO YOU FEEL? | VERY BAD | BAD | GOOD | VERY GOOD |
| HOW WELL ARE YOU MANAGING YOUR DISEASE? | VERY BADLY | BADLY | WELL | VERY WELL |
| HOW HARD IS IT FOR YOU TO FOLLOW YOUR TREATMENT PLAN? | VERY HARD | HARD | EASY | VERY EASY |
| HOW HARD IS IT FOR YOU TO CONTROL YOUR BLOOD SUGAR? | VERY HARD | HARD | EASY | VERY EASY |

SELECT DEVICE TYPE(S)

☒ GLUCOSE METER   ☐ RESPIRATORY FLOW METER   ☐ BP CUFF

CONNECTION TIME: 03:00 ▽   CREATE SCRIPT   CANCEL

*FIG. 5*

NUMBER: 9001 {LF}

LED: 1 {LF}

ZAP: {LF}

CLS: {LF}

DISPLAY: ANSWER QUERIES NOW?
        PRESS ANY BUTTON TO START {LF}

WAIT: {LF}

CLS: {LF}

DISPLAY: HOW DO YOU FEEL?

VERY           VERY
     BAD   BAD   GOOD  GOOD {LF}

INPUT: OOOO {LF}

CLS: {LF}

DISPLAY: HOW WELL ARE YOU
        MANAGING YOUR DISEASE?
        VERY              VERY
        WELL   BADLY  WELL  WELL {LF}

INPUT: OOOO {LF}

CLS: {LF}

DISPLAY: HOW HARD IS IT FOR YOU TO
        FOLLOW YOUR TREATMENT PLAN?
        VERY              VERY
        HARD   HARD  EASY  EASY {LF}

INPUT: OOOO {LF}

CLS: {LF}

DISPLAY: HOW HARD IS IT FOR YOU TO
        CONTROL YOUR BLOOD SUGAR?
        VERY              VERY
        HARD   HARD  EASY  EASY {LF}

*FIG. 6A*

INPUT: OOOO {LF}

CLS: {LF}

DISPLAY: CONNECT GLUCOSE METER
AND PRESS ANY BUTTON
WHEN FINISHED {LF}

WAIT: {LF}

CLS: {LF}

DISPLAY: COLLECTING MEASUREMENTS {LF}

COLLECT: GLUCOSE_METER {LF}

CLS: {LF}

DISPLAY: CONNECT APPARATUS TO
TELEPHONE JACK AND
PRESS ANY BUTTON
WHEN FINISHED {LF}

WAIT: {LF}

LED: 0 {LF}

CLS: {LF}

DELAY: 03:00 {LF}

DISPLAY: CONNECTING TO SERVER {LF}

CONNECT: {LF}

{EOF}

*FIG. 6B*

NETWORKED SYSTEM FOR INTERACTIVE COMMUNICATION AND REMOTE MONITORING OF INDIVIDUALS

RELATED APPLICATION INFORMATION

This application is a continuation in part of application Ser. No. 08/847,009 filed Apr. 30, 1997 now U.S. Pat. No. 5,897,493. This application also claims priority from provisional application Ser. No. 60/041,746 filed Mar. 28, 1997 and from provisional application Ser. No. 60/041,751 filed Mar. 28, 1997. This application also claims priority from an application with Ser. No. 09/201,323 entitled "Leveraging Interactions with a Community of Individuals", filed Nov. 30, 1998 and from an application with Ser. No. 09/274,433 entitled "Client-Initiated Leveraged Interaction with Providers", filed Mar. 22, 1999. All of the above named applications are hereby incorporated by reference.

FIELD OF THE INVENTION

The present invention relates generally to communication systems for remote monitoring of individuals, and in particular to a networked system for remotely monitoring individuals and for communicating information to the individuals through the use of script programs.

BACKGROUND OF THE INVENTION

In the United States alone, over 100 million people have chronic health conditions, accounting for an estimated $700 billion in annual medical costs. In an effort to control these medical costs, many healthcare providers have initiated outpatient or home healthcare programs for their patients. The potential benefits of these programs are particularly great for chronically ill patients who must treat their diseases on a daily basis. However, the success of these programs is dependent upon the ability of the healthcare providers to monitor the patients remotely to avert medical problems before they become complicated and costly. Unfortunately, no convenient and cost effective monitoring system exists for the patients who have the greatest need for monitoring, the poor and the elderly.

Prior attempts to monitor patients remotely have included the use of personal computers and modems to establish communication between patients and healthcare providers. However, computers are too expensive to give away and the patients who already own computers are only a small fraction of the total population. Further, the patients who own computers are typically young, well educated, and have good healthcare coverage. Thus, these patients do not have the greatest unmet medical needs. The patients who have the greatest unmet medical needs are the poor and elderly who do not own computers or who are unfamiliar with their use.

Similar attempts to establish communication between patients and healthcare providers have included the use of the Internet and internet terminals. Although internet terminals are somewhat less costly than personal computers, they are still too expensive to give away to patients. Moreover, monthly on-line access charges are prohibitive for poor patients.

Other attempts to monitor patients remotely have included the use of medical monitoring devices with built-in modems. Examples of such monitoring devices include blood glucose meters, respiratory flow meters, and heart rate monitors. Unfortunately, these monitoring devices are only designed to collect physiological data from the patients. They do not allow flexible and dynamic querying of the patients for other information, such as quality of life measures or psychosocial variables of illness.

Prior attempts to monitor patients remotely have also included the use of interactive telephone or video response systems. Such interactive systems are disclosed in U.S. Pat. No. 5,39.0,238 issued to Kirk et al. on Feb. 14, 1995, U.S. Pat. No. 5,434,611 issued to Tamura on Jul. 18, 1995, and U.S. Pat. No. 5,441,047 issued to David et al. on Aug. 15, 1995. One disadvantage of these systems is that they either require a patient to call in to a central facility to be monitored or require the central facility to call the patient according to a rigid monitoring schedule.

If the patients are required to call the central facility, only the compliant patients will actually call regularly to be monitored. Non-compliant patients will typically wait until an emergency situation develops before contacting their healthcare provider, thus defeating the purpose of the monitoring system. If the central facility calls each patient according to a monitoring schedule, it is intrusive to the patient's life and resistance to the monitoring grows over time.

Another disadvantage of these conventional interactive response systems is that they are prohibitively expensive for poor patients. Further, it is difficult to identify each patient uniquely using these systems. Moreover, these systems are generally incapable of collecting medical data from monitoring devices, such as blood glucose meters, respiratory flow meters, or heart rate monitors.

OBJECTS AND ADVANTAGES OF THE INVENTION

In view of the above, it is an object of the present invention to provide a simple and inexpensive system for remotely monitoring patients and for communicating information to the patients. It is another object of the invention to provide a system which allows flexible and dynamic querying of the patients. It is a further object of the invention to provide a system which combines querying of patients with medical device monitoring in the same monitoring session. Another object of the invention is to provide a monitoring system which incurs lower communications charges than those incurred by conventional monitoring systems. A further object of the invention is to provide a monitoring system which may be used at any time convenient for a patient.

These and other objects and advantages will become more apparent after consideration of the ensuing description and the accompanying drawings.

SUMMARY

The invention presents a networked system for remotely monitoring an individual and for communicating information to the individual. The system includes a server and a remote interface for entering in the server a set of queries to be answered by the individual. The server is preferably a world wide web server and the remote interface is preferably a personal computer or network terminal connected to the web server via the Internet. The system also includes a remotely programmable apparatus for interacting with the individual. The apparatus is connected to the server via a communication network, preferably the Internet. The apparatus interacts with the individual in accordance with a script program received from the server.

The server includes a script generator for generating the script program from the queries entered through the remote interface. The script program is executable by the apparatus to communicate the queries to the individual, to receive responses to the queries, and to transmit the responses from the apparatus to the server. The server also includes a database connected to the script generator for storing the script program and the responses to the queries.

The apparatus has a communication device, such as a modem, for receiving the script program from the server and for transmitting the responses to the server. The apparatus also has a user interface for communicating the queries to the individual and for receiving the responses to the queries. In the preferred embodiment, the user interface includes a display for displaying the queries and user input buttons for entering the responses to the queries. In an alternative embodiment, the user interface includes a speech synthesizer for audibly communicating the queries and a speech recognizer for receiving spoken responses to the queries.

The apparatus also includes a memory for storing the script program and the responses to the queries. The apparatus further includes a microprocessor connected to the communication device, the user interface, and the memory. The microprocessor executes the script program to communicate the queries to the individual, to receive the responses to the queries, and to transmit the responses to the server through the communication network.

In the preferred embodiment, the system also includes at least one monitoring device for producing measurements of a physiological condition of the individual and for transmitting the measurements to the apparatus. The apparatus further includes a device interface connected to the microprocessor for receiving the measurements from the monitoring device. The measurements are stored in the memory and transmitted to the server with the responses to the queries. The server also preferably includes a report generator connected to the database for generating a report of the measurements and responses. The report is displayed on the remote interface.

BRIEF DESCRIPTION OF THE DRAWINGS

FIG. 5 is a script entry screen according to the preferred embodiment of the invention.

FIG. 6A is a listing of a sample script program according to the preferred embodiment of the invention.

FIG. 6B is a continuation of the listing of FIG. 6A.

DETAILED DESCRIPTION

The invention presents a system and method for remotely monitoring individuals and for communicating information to the individuals. In a preferred embodiment of the invention, the individuals are patients and the system is used to collect data relating to the health status of the patients. However, it is to be understood that the invention is not limited to remote monitoring of patients. The system and method of the invention may be used for any type of remote monitoring application. The invention may also be implemented as an automated messaging system for communicating information to individuals, as will be discussed in an alternative embodiment below.

Figure 1:
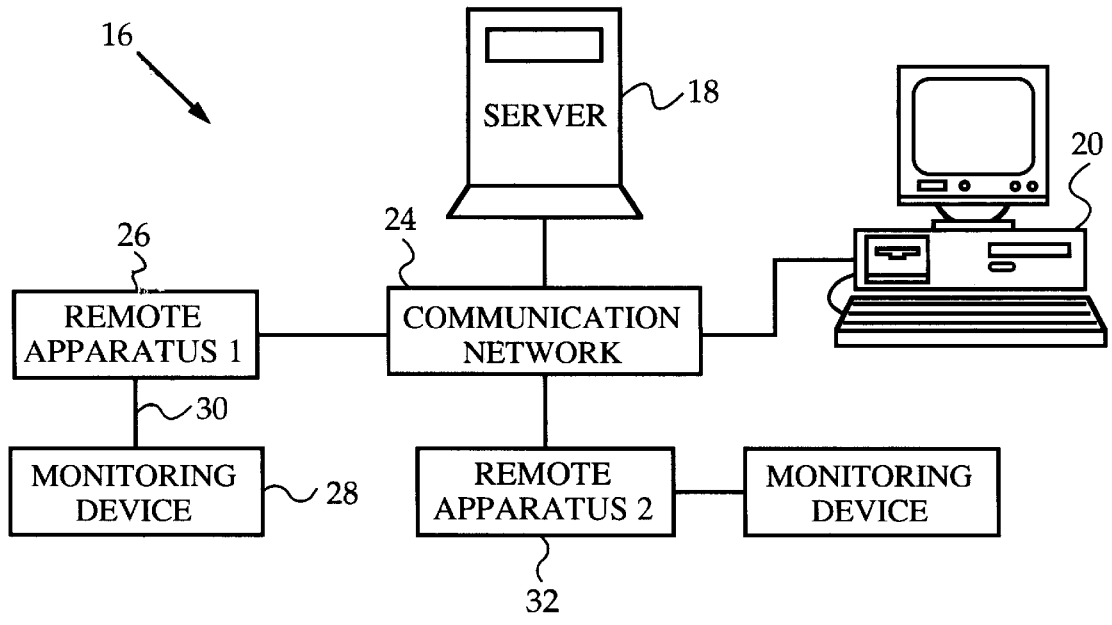
FIG. 1 is a block diagram of a networked system according to a preferred embodiment of the invention.

A preferred embodiment of the invention is illustrated in FIGS. 1–12. Referring to FIG. 1, a networked system 16 includes a server 18 and a workstation 20 connected to server 18 through a communication network 24. Server 18 is preferably a world wide web server and communication network 24 is preferably the Internet. It will be apparent to one skilled in the art that server 18 may comprise a single stand-alone computer or multiple computers distributed throughout a network. Workstation 20 is preferably a personal computer, remote terminal, or web TV unit connected to server 18 via the Internet. Workstation 20 functions as a remote interface for entering in server 18 messages and queries to be communicated to the patients.

System 16 also includes first and second remotely programmable apparatuses 26 and 32 for monitoring first and second patients, respectively. Each apparatus 26/32 is designed to interact with a patient in accordance with script programs received from server 18. Each apparatus 26/32 is in communication with server 18 through communication network 24, preferably the Internet. Alternatively, each apparatus 26/32 may be placed in communication with server 18 via wireless communication networks, cellular networks, telephone networks, or any other network which allows each apparatus 26/32 to exchange data with server 18. For clarity of illustration, only two apparatuses 26 and 32 are shown in FIG. 1. It is to be understood that system 16 may include any number of remotely programmable apparatuses for monitoring any number of patients.

In the preferred embodiment, each patient to be monitored is also provided with a monitoring device 28. Monitoring device 28 is designed to produce measurements of a physiological condition of the patient, record the measurements, and transmit the measurements to the patient's remotely programmable apparatus through a standard connection cable 30. Examples of suitable monitoring devices 28 include blood glucose meters, respiratory flow meters, blood pressure cuffs, electronic weight scales, and pulse rate monitors. Such monitoring devices are well known in the art. The specific type of monitoring device 28 provided to each patient is dependent upon the patient's disease. For example, diabetes patients are provided with a blood glucose meter for measuring blood glucose concentrations, asthma patients are provided with respiratory flow meters for measuring peak flow rates, obesity patients are provided with weight scales, etc.

Figure 2:
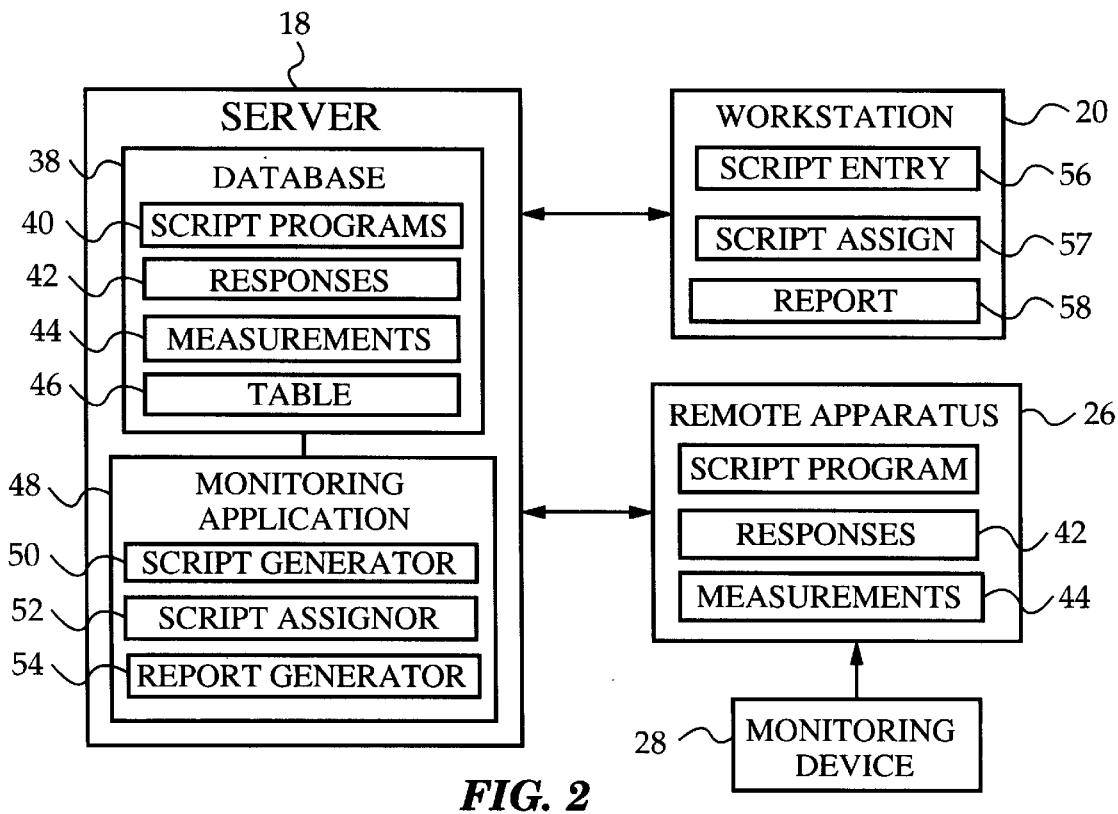
FIG. 2 is a block diagram illustrating the interaction of the components of the system of FIG. 1.

FIG. 2 shows server 18, workstation 20, and apparatus 26 in greater detail. Server 18 includes a database 38 for storing script programs 40. Script programs 40 are executed by each apparatus e.g., 26/32, to communicate queries and messages to a patient, receive responses 42 to the queries, collect monitoring device measurements 44, and to transmit responses 42 and measurements 44 to server 18. Database 38 is designed to store responses 42 and measurements 44. Database 38 further includes a look-up table 46. Table 46 contains a list of the patients to be monitored, and for each patient, a unique patient identification code and a respective pointer to the script program assigned to the patient. Each remotely programmable apparatus, e.g., 26/32, is designed to execute assigned script programs 40 received from server 18.

Figure 3:
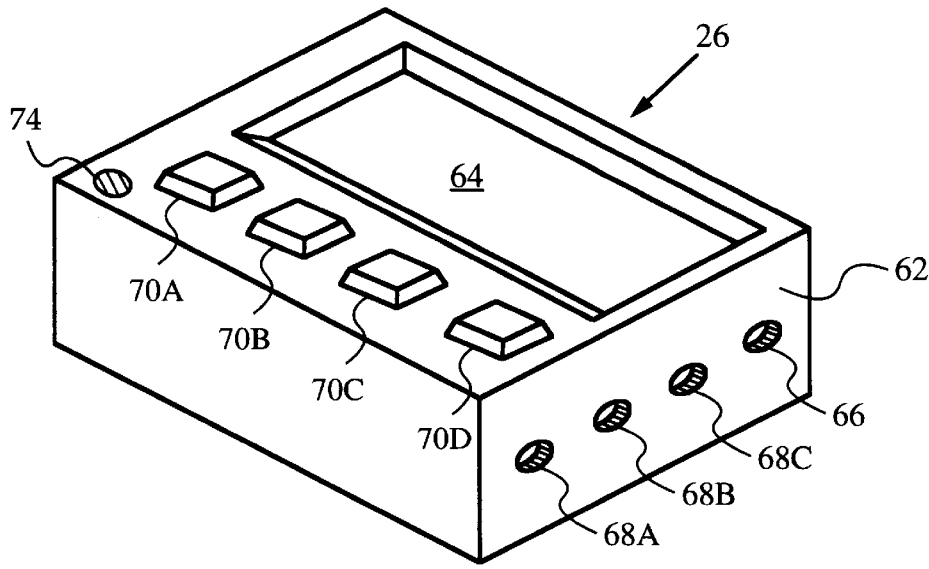
FIG. 3 is a perspective view of a remotely programmable apparatus of the system of FIG. 1.
Figure 4:
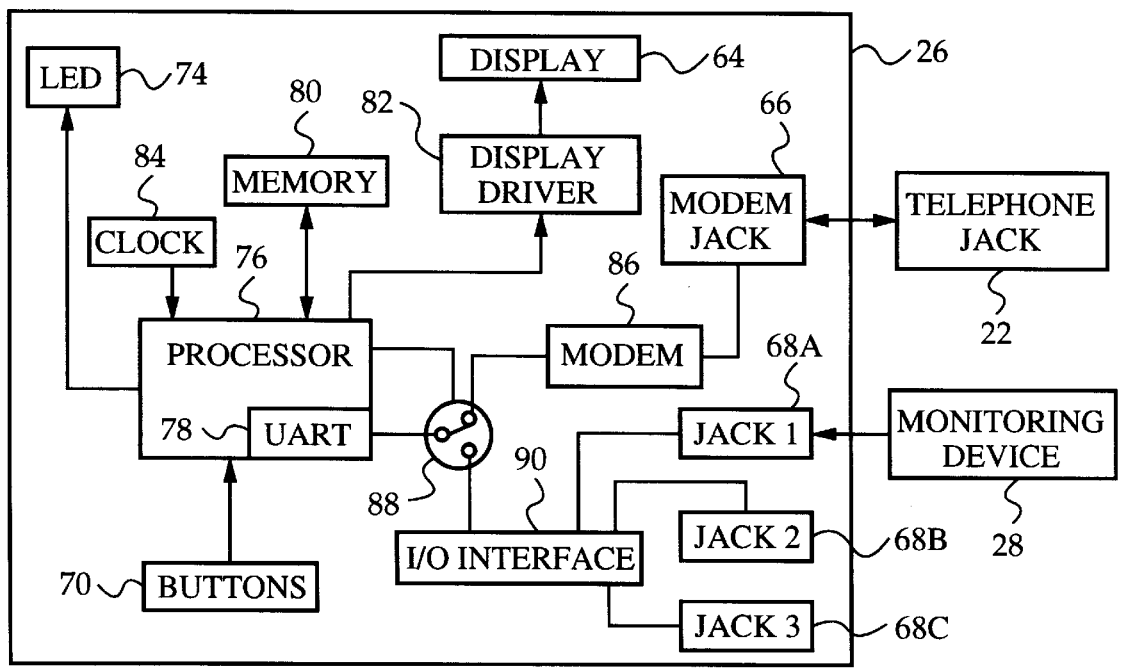
FIG. 4 is a block diagram illustrating the components of the apparatus of FIG. 3.

FIGS. 3–4 show the structure of each remotely programmable apparatus according to the preferred embodiment. For clarity, only remotely programmable apparatus 26 is shown since each remotely programmable apparatus of the preferred embodiment has substantially identical structure to apparatus 26. Referring to FIG. 3, apparatus 26 includes a housing 62. Housing 62 is sufficiently compact to enable apparatus 26 to be hand-held and carried by a patient. Apparatus 26 also includes a display 64 for displaying queries and prompts to the patient. In the preferred embodiment, display 64 is a liquid crystal display (LCD).

Four user input buttons 70A, 70B, 70C, and 70D are located adjacent display 64. User input buttons 70A–D are for entering in apparatus 26 responses 42 to the queries and prompts. In the preferred embodiment, user input buttons 70A–D are momentary contact push buttons. In alternative embodiments, user input buttons 70A–D may be replaced by switches, keys, a touch sensitive display screen, or any other data input device.

Three monitoring device jacks 68A, 68B, and 68C are located on a surface of housing 62. Device jacks 68A–C are for connecting apparatus 26 to a number of monitoring devices 28, such as blood glucose meters, respiratory flow meters, or blood pressure cuffs, through respective connection cables 30 (not shown in FIG. 3). Apparatus 26 also includes a modem jack 66 for connecting apparatus 26 to a telephone jack through a standard connection cord (not shown). Apparatus 26 further includes a visual indicator, such as a light emitting diode (LED) 74. LED 74 is for visually notifying the patient that he or she has unanswered queries stored in apparatus 26.

FIG. 4 is a schematic block diagram illustrating the components of apparatus 26 in greater detail. Apparatus 26 includes a microprocessor 76 and a memory 80 connected to microprocessor 76. Memory 80 is preferably a non-volatile memory, such as a serial EEPROM. Memory 80 stores script programs 40 received from server 18, measurements 44 received from monitoring device 28, responses 42 to queries, and the patient's unique identification code. Microprocessor 76 also includes built-in read only memory (ROM) which stores firmware for controlling the operation of apparatus 26. The firmware includes a script interpreter used by microprocessor 76 to execute script programs 40. The script interpreter interprets script commands which are executed by microprocessor 76. Specific techniques for interpreting and executing script commands in this manner are well known in the art.

Microprocessor 76 is preferably connected to memory 80 using a standard two-wire I$^2$C interface. Microprocessor 76 is also connected to user input buttons 70, LED 74, a clock 84, and a display driver 82. Clock 84 indicates the current date and time to microprocessor 76. For clarity of illustration, clock 84 is shown as a separate component, but is preferably built into microprocessor 76. Display driver 82 operates under the control of microprocessor 76 to display information on display 64. Microprocessor 76 is preferably a PIC 16C65 processor which includes a universal asynchronous receiver transmitter (UART) 78. UART 78 is for communicating with a modem 86 and a device interface 90. A CMOS switch 88 under the control of microprocessor 76 alternately connects modem 86 and interface 90 to UART 78.

Modem 86 is connected to a telephone jack 22 through modem jack 66. Modem 86 is for exchanging data with server 18 through communication network 24. The data includes script programs 40 which are received from server 18 as well as responses 42 to queries, device measurements 44, script identification codes, and the patient's unique identification code which modem 86 transmits to server 18. Modem 86 is preferably a complete 28.8 K modem commercially available from Cermetek, although any suitable modem may be used.

Device interface 90 is connected to device jacks 68A, 68B, and 68C. Device interface 90 is for interfacing with a number of monitoring devices 28, such as blood glucose meters, respiratory flow meters, blood pressure cuffs, weight scales, or pulse rate monitors, through device jacks 68A–C. Device interface 90 operates under the control of microprocessor 76 to collect measurements 44 from monitoring devices 28 and to output the measurements to microprocessor 76 for storage in memory 80. In the preferred embodiment, interface 90 is a standard RS232 interface. For simplicity of illustration, only one device interface 90 is shown in FIG. 4. However, in alternative embodiments, apparatus 26 may include multiple device interfaces to accommodate monitoring devices which have different connection standards.

Referring again to FIG. 2, server 18 includes a monitoring application 48. Monitoring application 48 is a controlling software application executed by server 18 to perform the various functions described below. Application 48 includes a script generator 50, a script assignor 52, and a report generator 54. Script generator 50 is designed to generate script programs 40 from script information entered through workstation 20. The script information is entered through a script entry screen 56. In the preferred embodiment, script entry screen 56 is implemented as a web page on server 18. Workstation 20 includes a web browser for accessing the web page to enter the script information.

FIG. 5 illustrates script entry screen 56 as it appears on workstation 20. Screen 56 includes a script name field 92 for specifying the name of a script program to be generated. Screen 56 also includes entry fields 94 for entering a set of queries to be answered by a patient. Each entry field 94 has corresponding response choice fields 96 for entering response choices for the query. Screen 56 further includes check boxes 98 for selecting a desired monitoring device 28, such as a blood glucose meter, respiratory flow meter, or blood pressure cuff, from which to collect measurements 44.

Screen 56 additionally includes a connection time field 100 for specifying a prescribed connection time at which each apparatus 26 executing the script is to establish a subsequent communication link to server 18. The connection time is preferably selected to be the time at which communication rates are the lowest, such as 3:00 AM. Screen 56 also includes a CREATE SCRIPT button 102 for instructing script generator 50 to generate a script program 40 from the information entered in screen 56. Screen 56 further includes a CANCEL button 104 for canceling the information entered in screen 56.

In the preferred embodiment, each script program 40 created by script generator 50 conforms to the standard file format used on UNIX systems. In the standard file format, each command is listed in the upper case and followed by a colon. Every line in the script program 40 is terminated by a linefeed character {LF}, and only one command is placed on each line. The last character in the script program 40 is a UNIX end of file character {EOF}. Table 1 shows an exemplary listing of script commands used in the preferred embodiment of the invention.

TABLE 1

SCRIPT COMMANDS

| Command | Description |
| --- | --- |
| CLS: {LF} | Clear the display. |
| ZAP: {LF} | Erase from memory the last set of query responses recorded. |
| LED: b{LF} | Turn the LED on or off, where b is a binary digit of 0 or 1. An argument of 1 turns on the LED, and an argument of 0 turns off the LED. |
| DISPLAY: {chars} {LF} | Display the text following the DISPLAY command. |
| INPUT: mmmm{LF} | Record a button press. The m's represent a button mask pattern for each of the four input buttons. Each m contains an "X" for disallowed buttons or an "O" for allowed buttons. For example, INPUT: OXOX{LF} allows the user to press either button #1 or #3. |
| WAIT: {LF} | Wait for any one button to be pressed, then continue executing the script program. |
| COLLECT: device{LF} | Collect measurements from the monitoring device specified in the COLLECT command. The user is preferably prompted to connect the specified monitoring device to the apparatus and press a button to continue. |
| NUMBER: aaaa{LF} | Assign a script identification code to the script program. The script identification code from the most recently executed NUMBER statement is subsequently transmitted to the server along with the query responses and device measurements. The script identification code identifies to the server which script program was most recently executed by the remote apparatus. |
| DELAY: t{LF} | Wait until time t specified in the DELAY command, usually the prescribed connection time. |
| CONNECT: {LF} | Perform a connection routine to establish a communication link to the server, transmit the patient identification code, query responses, device measurements, and script identification code to the server, and receive and store a new script program. When the server instructs the apparatus to disconnect, the script interpreter is restarted, allowing the new script program to execute. |

The script commands illustrated in Table 1 are representative of the preferred embodiment and are not intended to limit the scope of the invention. After consideration of the ensuing description, it will be apparent to one skilled in the art many other suitable scripting languages and sets of script commands may be used to implement the invention.

Script generator 50 preferably stores a script program template which it uses to create each script program 40. To generate a script program 40, script generator 50 inserts into the template the script information entered in screen 56. For example, FIGS. 6A–6B illustrate a sample script program 40 created by script generator 50 from the script information shown in FIG. 5.

The script program 40 includes display commands to display the queries and response choices entered in fields 94 and 96, respectively. The script program 40 also includes input commands to receive responses 42 to the queries. The script program 40 further includes a collect command to collect device measurements 44 from the monitoring device 28 specified in check boxes 98. The script program 40 also includes commands to establish a subsequent communication link to server 18 at the connection time specified in field 100 FIG. 5. The steps included in the script program 40 are also shown in the flow chart of FIGS. 12A–12B and will be discussed in the operation section below.

Referring again to FIG. 2, script assignor 52 is for assigning script programs 40 to the patients. Script programs 40 are assigned in accordance with script assignment information entered through workstation 20. The script assignment information is entered through a script assignment screen 57, which is preferably implemented as a web page on server 18.

Figure 7:
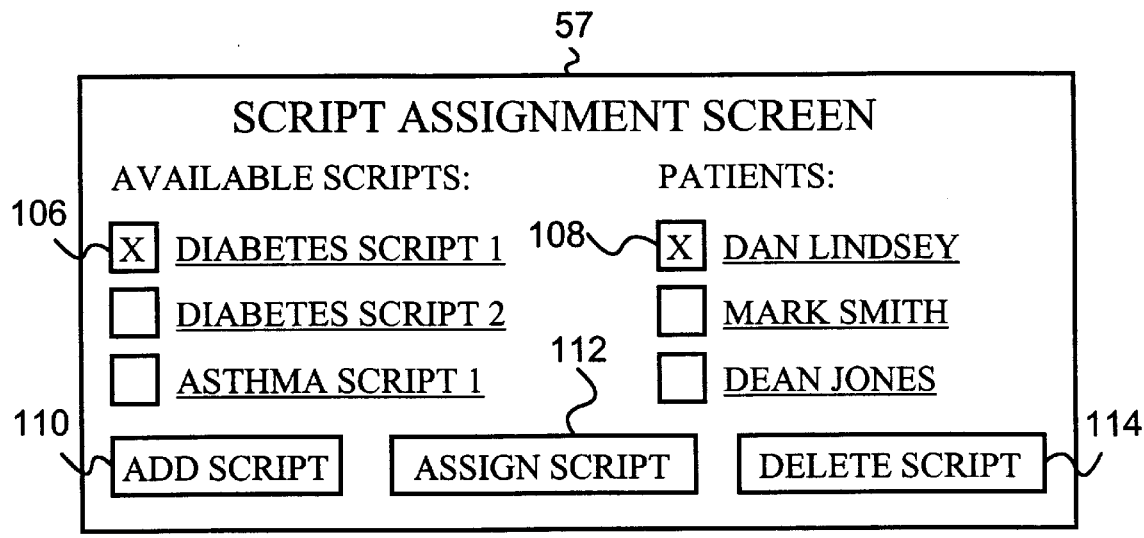
FIG. 7 is a script assignment screen according to the preferred embodiment of the invention.

FIG. 7 illustrates a sample script assignment screen 57 as it appears on workstation 20. Screen 57 includes check boxes 106 for selecting a script program 40 to be assigned, and check boxes 108 for selecting the patients to whom the script program is to be assigned. Screen 57 also includes an ASSIGN SCRIPT button 112 for entering the assignments. When button 112 is pressed, script assignor 52 creates and stores for each patient selected in check boxes 108 a respective pointer to the script program 40 selected in check boxes 106. Each pointer is stored in the patient look-up table 46 of database 38. Screen 57 further includes an ADD SCRIPT button 110 for accessing the script entry screen and a DELETE SCRIPT button 114 for deleting a script program 40.

Figure 10:
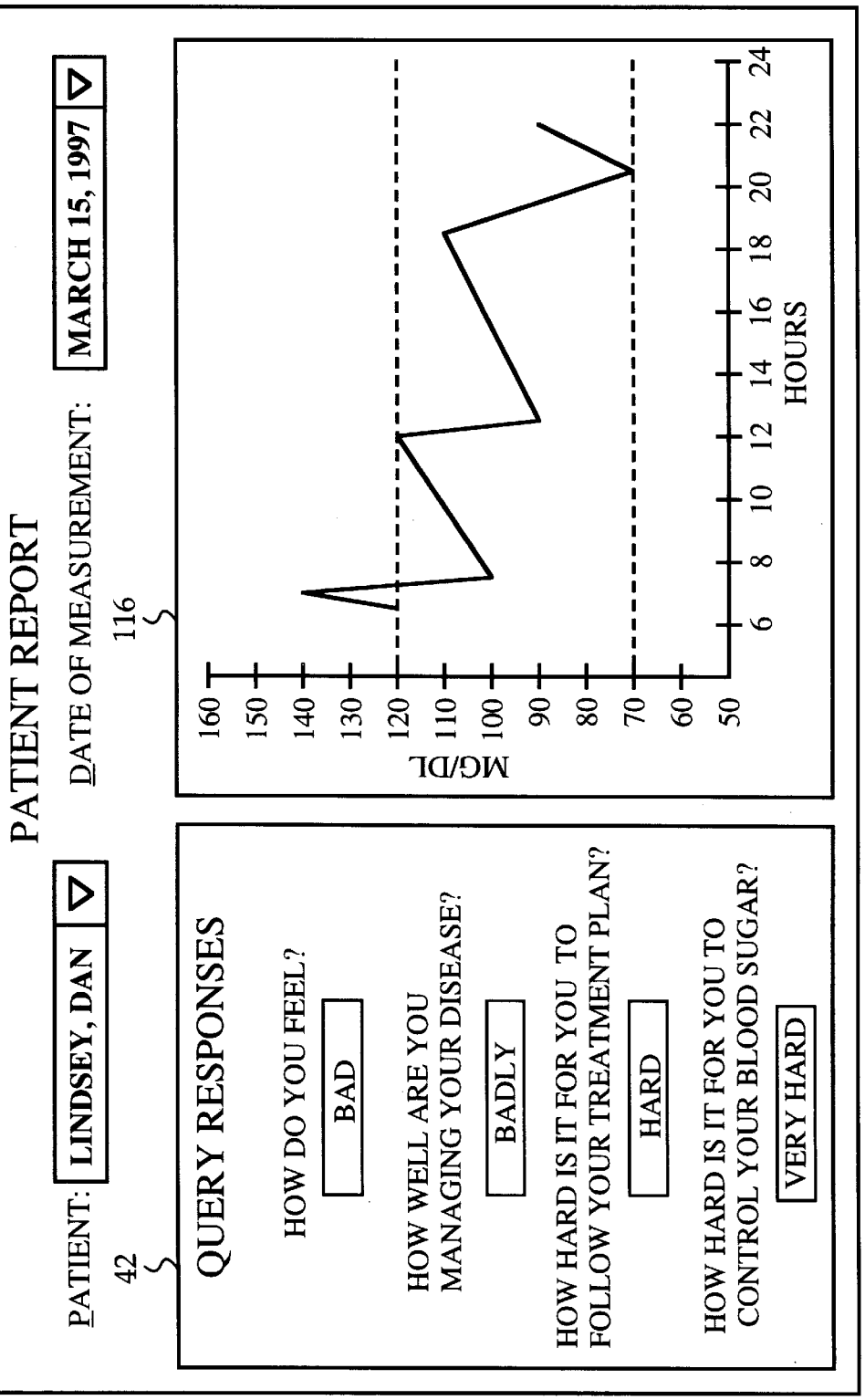
FIG. 10 is a sample report displayed on a workstation of the system of FIG. 1.
Figure 11A:
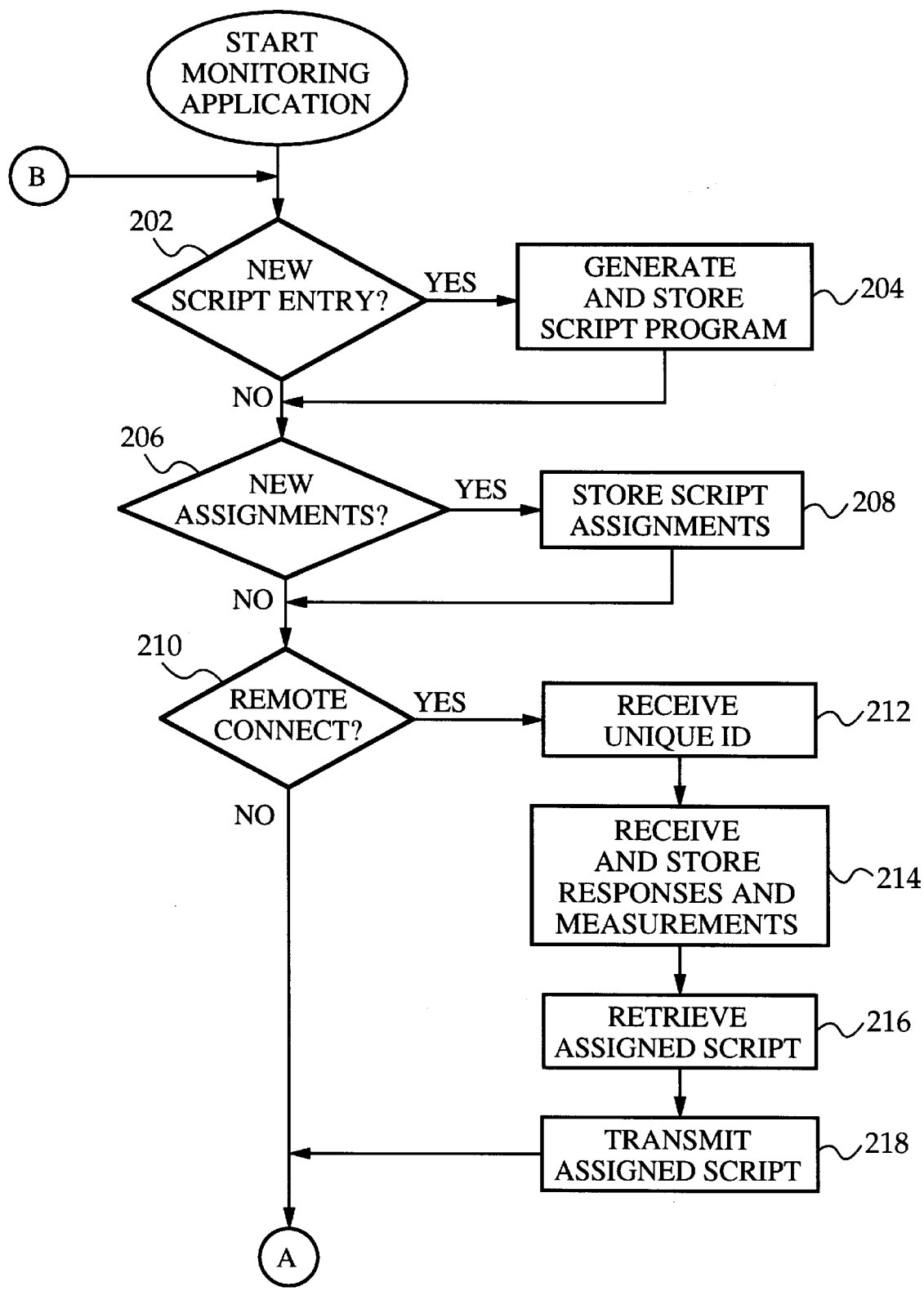
FIG. 11A is a flow chart illustrating the steps included in a monitoring application executed by the server of FIG. 1 according to the preferred embodiment of the invention.
Figure 11B:
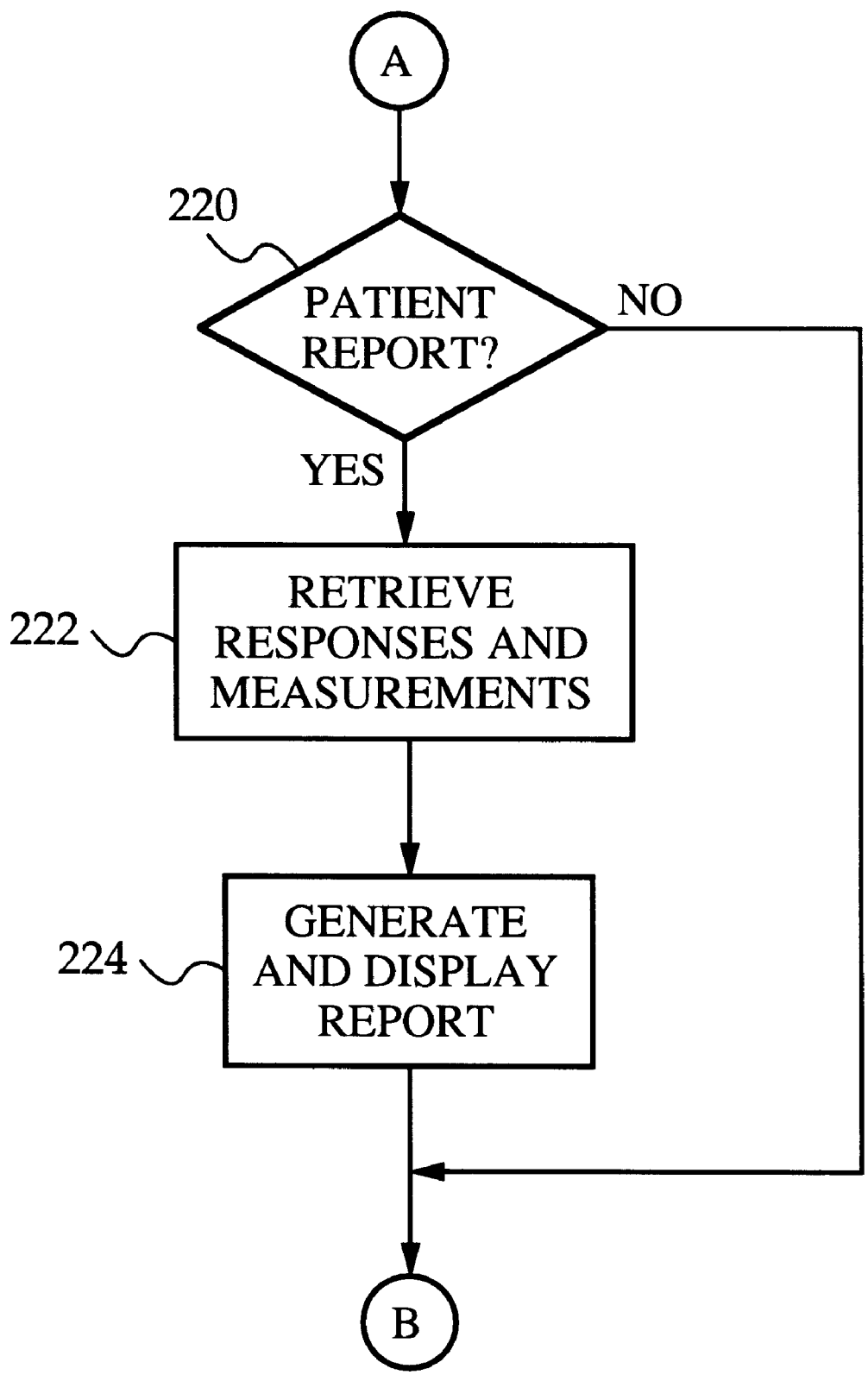
FIG. 11B is a continuation of the flow chart of FIG. 11A.

Referring again to FIG. 2, report generator 54 is designed to generate a patient report 58 from responses 42 and device measurements 44 received in server 18. Patient report 58 is displayed on workstation 20. FIG. 10 shows a sample patient report 58 produced by report generator 54 for a selected patient. Patient report 58 includes a graph 116 of the device measurements 44 received from the patient, as well as a listing of responses 42 received from the patient. Specific techniques for writing a report generator program to display data in this manner are well known in the art.

The operation of the preferred embodiment is illustrated in FIGS. 1–12. FIG. 11A is a flow chart illustrating steps included in the monitoring application executed by server 18. FIG. 11B is a continuation of the flow chart of FIG. 11A. In step 202, server 18 determines if new script information has been entered through script entry screen 56. If new script information has not been entered, server 18 proceeds to step 206. If new script information has been entered, server 18 proceeds to step 204.

As shown in FIG. 5, the script information includes a set of queries, and for each of the queries, corresponding response choices. The script information also includes a selected monitoring device type from which to collect device measurements 44. The script information further includes a prescribed connection time for each apparatus to establish a subsequent communication link to server 18. The script information is generally entered in server 18 by a healthcare provider, such as the patients' physician or case manager. Of course, any person desiring to communicate with the patients may also be granted access to server 18 to create and assign script programs 40. Further, it is to be understood that system 16 may include any number of remote interfaces for entering script generation and script assignment information in server 18.

In step 204, script generator 50 generates a script program from the information entered in screen 56. The script program is stored in database 38. Steps 202 and 204 are preferably repeated to generate multiple script programs, e.g. a script program for diabetes patients, a script program for asthma patients, etc. Each script program corresponds to a respective one of the sets of queries entered through script entry screen 56. Following step 204, server 18 proceeds to step 206.

In step 206, server 18 determines if new script assignment information has been entered through assignment screen 57. If new script assignment information has not been entered, server 18 proceeds to step 210. If new script assignment information has been entered, server 18 proceeds to step 208. As shown in FIG. 7, the script programs are assigned to each patient by selecting a script program through check boxes 106, selecting the patients to whom the selected script program is to be assigned through check boxes 108, and pressing the ASSIGN SCRIPT button 112. When button 112 is pressed, script assignor 52 creates for each patient selected in check boxes 108 a respective pointer to the script program selected in check boxes 106. In step 208, each pointer is stored in look-up table 46 of database 38. Following step 208, server 18 proceeds to step 210.

In step 210, server 18 determines if any of the apparatuses are remotely connected to the server. Each patient to be monitored is preferably provided with his or her own remotely programmable apparatus which has the patient's unique identification code stored therein. Each patient is thus uniquely associated with a respective one of the apparatuses. If none of the apparatuses is connected, server 18 proceeds to step 220.

If an apparatus is connected, server 18 receives from the apparatus the patient's unique identification code in step 212. In step 214, server 18 receives from the apparatus the query responses 42, device measurements 44, and script identification code recorded during execution of a previously assigned script program. The script identification code identifies to server 18 which script program was executed by the apparatus to record the query responses 42 and device measurements 44. The responses, device measurements, and script identification code are stored in database 38.

In step 216, server 18 uses the patient identification code to retrieve from table 46 the pointer to the script program assigned to the patient. Server 18 then retrieves the assigned script program from database 38. In step 218, server 18 transmits the assigned script program to the patient's remotely programmable apparatus through communication network 24. Following step 218, server 18 proceeds to step 220.

In step 220, server 18 determines if a patient report request has been received from workstation 20. If no report request has been received, server 18 returns to step 202. If a report request has been received for a selected patient, server 18 retrieves from database 38 the measurements 44 and query responses 42 last received from the patient, step 222. In step 224, server 18 generates and displays patient report 58 on workstation 20. As shown in FIG. 10, report 58 includes the device measurements 44 and query responses 42 last received from the patient. Following step 224, server 18 returns to step 202.

Figure 12A:
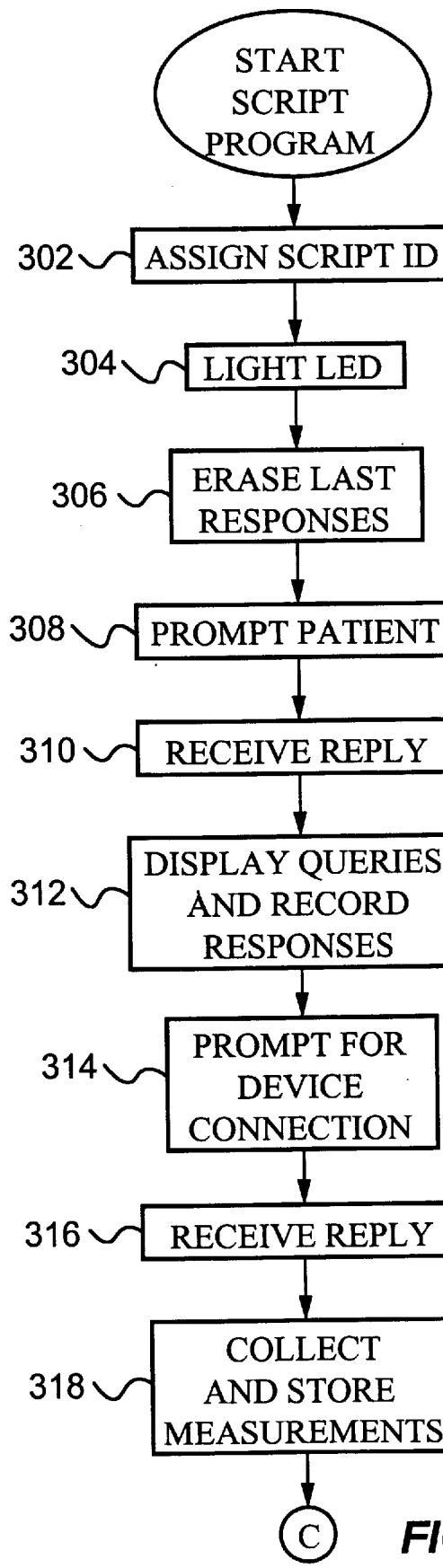
FIG. 12A is a flow chart illustrating the steps included in the script program of FIGS. 6A–6B.
Figure 12B:
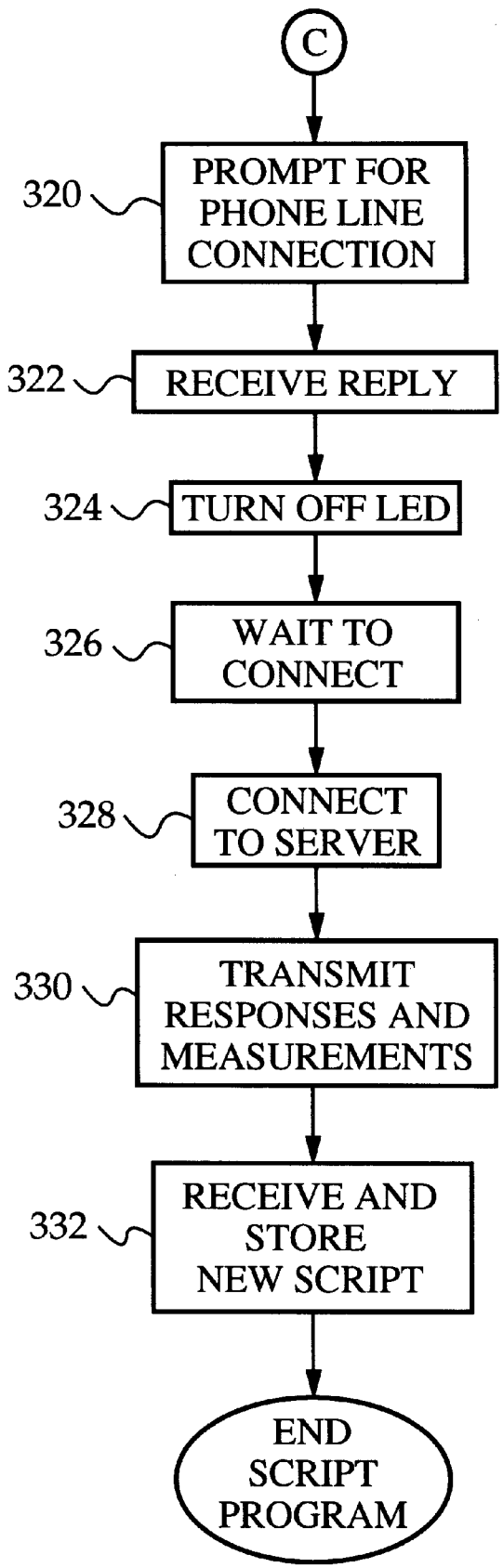
FIG. 12B is a continuation of the flow chart of FIG. 12A.

FIGS. 12A–12B illustrate the steps included in the script program executed by apparatus 26. Before the script program is received, apparatus 26 is initially programmed with the patient's unique identification code and the script interpreter used by microprocessor 76 to execute the script program. The initial programming may be achieved during manufacture or during an initial connection to server 18. Following initial programming, apparatus 26 receives from server 18 the script program assigned to the patient associated with apparatus 26. The script program is received by modem 86 through a first communication link and stored in memory 80.

In step 302, microprocessor 76 assigns a script identification code to the script program and stores the script identification code in memory 80. The script identification code is subsequently transmitted to server 18 along with the query responses 42 and device measurements 44 to identify to server 18 which script program was most recently executed by apparatus 26. In step 304, microprocessor 76 lights LED 74 to notify the patient that he or she has unanswered queries stored in apparatus 26. LED 74 preferably remains lit until the queries are answered by the patient. In step 306, microprocessor 76 erases from memory 80 the last set of query responses recorded.

In step 308, microprocessor 76 prompts the patient by displaying on display 64 "ANSWER QUERIES NOW? PRESS ANY BUTTON TO START". In step 310, microprocessor 76 waits until a reply to the prompt is received from the patient. When a reply is received, microprocessor 76 proceeds to step 312. In step 312, microprocessor 76 executes successive display and input commands to display the queries and response choices on display 64 and to receive responses to the queries.

Figure 8:
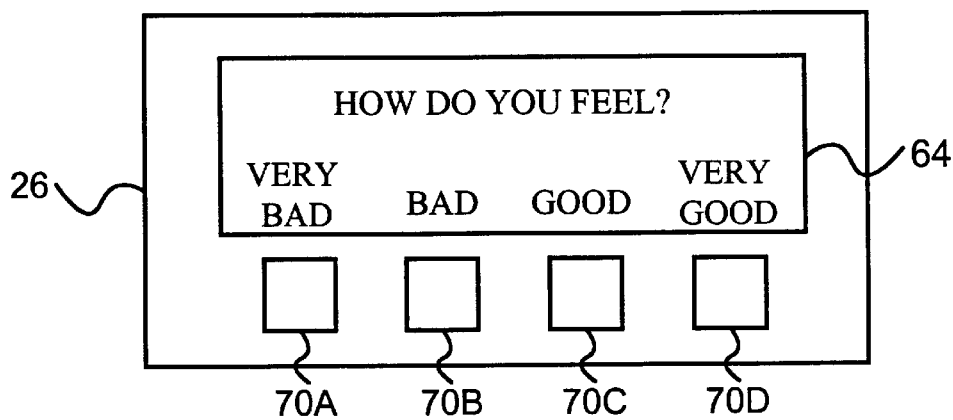
FIG. 8 is a sample query appearing on a display of the apparatus of FIG. 3.

FIG. 8 illustrates a sample query and its corresponding response choices as they appear on display 64. The response choices are positioned on display 64 such that each response choice is located proximate a respective one of input buttons 70A–D. In the preferred embodiment, each response choice is displayed immediately above a respective input button 70A–D. The patient presses the button 70A–D corresponding to his or her response. Microprocessor 76 stores each response in memory 80.

Figure 9:
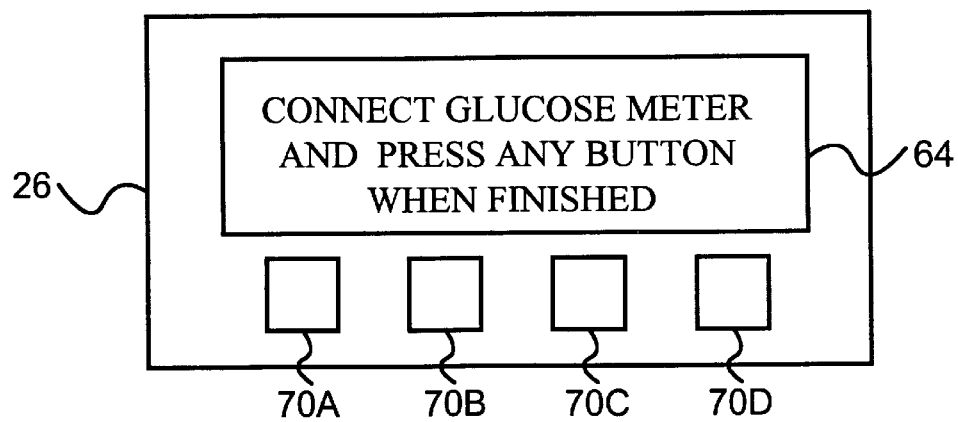
FIG. 9 is a sample prompt appearing on the display of the apparatus of FIG. 3.

In steps 314–318, microprocessor 76 executes commands to collect device measurements 44 from a selected monitoring device 28. The script program specifies the selected monitoring device from which to collect the measurements. In step 314, microprocessor 76 prompts the patient to connect the selected monitoring device 28, for example a blood glucose meter, to one of device jacks 68A–C. A sample prompt is shown in FIG. 9. In step 316, microprocessor 76 waits until a reply to the prompt is received from the patient. When a reply is received, microprocessor 76 proceeds to step 318. Microprocessor 76 also connects UART 78 to interface 90 through switch 88. In step 318, microprocessor 76 collects device measurements 44 from monitoring device 28 through interface 90. measurements 44 are stored in memory 80.

In step 320, microprocessor 76 prompts the patient to connect apparatus 26 to telephone jack 22 so that apparatus 26 may connect to server 18 at the prescribed connection time. In step 322, microprocessor 76 waits until a reply to the prompt is received from the patient. When a reply is received, microprocessor 76 turns off LED 74 in step 324. In step 326, microprocessor 76 waits until it is time to connect to server 18. Microprocessor 76 compares the connection time specified in the script program to the current time output by clock 84. When it is time to connect, microprocessor 76 connects UART 78 to modem 86 through switch 88.

In step 328, microprocessor 76 establishes a subsequent communication link between apparatus 26 and server 18 through modem 86 and communication network 24. If the connection fails for any reason, microprocessor 76 repeats step 328 to get a successful connection. In step 330, microprocessor 76 transmits the device measurements 44, query responses 42, script identification code, and patient identification code stored in memory 80 to server 18 through the subsequent communication link. In step 332, microprocessor 76 receives through modem 86 a new script program from server 18. The new script program is stored in memory 80 for subsequent execution by microprocessor 76. Following step 332, the script program ends.

One advantage of the monitoring system of the present invention is that it allows each patient to select a convenient time to respond to the queries, so that the monitoring system is not intrusive to the patient's schedule. A second advantage of the monitoring system is that it incurs very low communications charges because each remote apparatus connects to server 18 at times when communication rates are lowest. Moreover, the cost to manufacture each remote apparatus 26 is very low compared to personal computers or internet terminals, so that the monitoring system is highly affordable.

A third advantage of the monitoring system is that it allows each apparatus 26 to be programmed remotely through script programs 40. Patient surveys, connection times, display prompts, selected monitoring devices, patient customization, and other operational details of each apparatus 26 may be easily changed by transmitting a new script program 40 to apparatus 26. Moreover, each script program 40 may be easily created and assigned by remotely accessing server 18 through the Internet. Thus, the invention provides a powerful, convenient, and inexpensive system for remotely monitoring a large number of patients.

Figure 13:
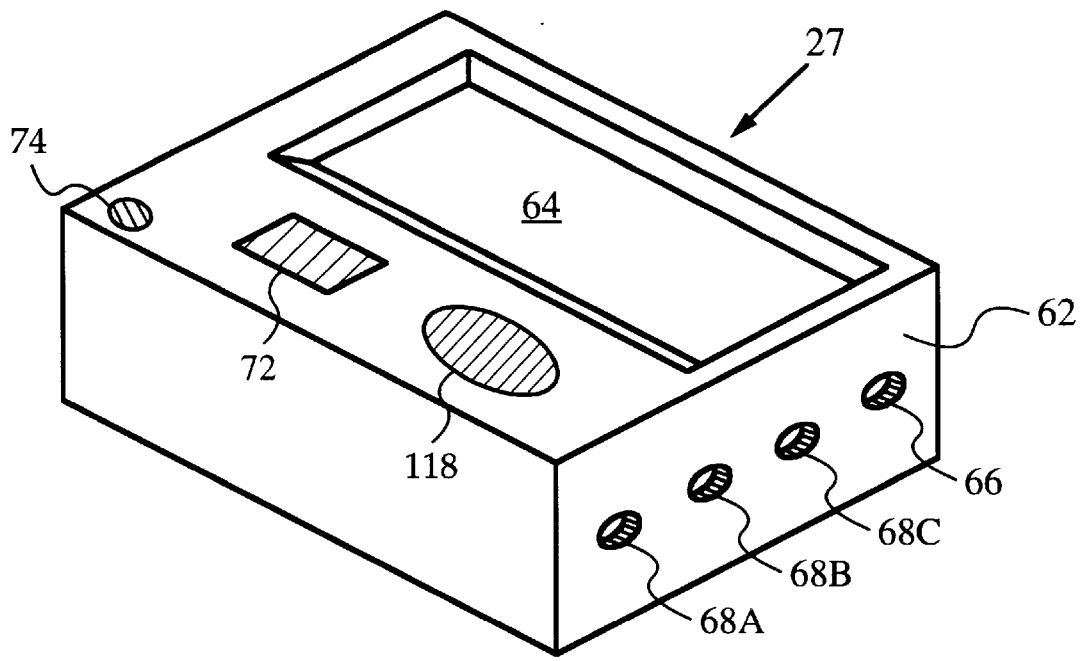
FIG. 13 is a perspective view of a remotely programmable apparatus according to a second embodiment of the invention.
Figure 14:
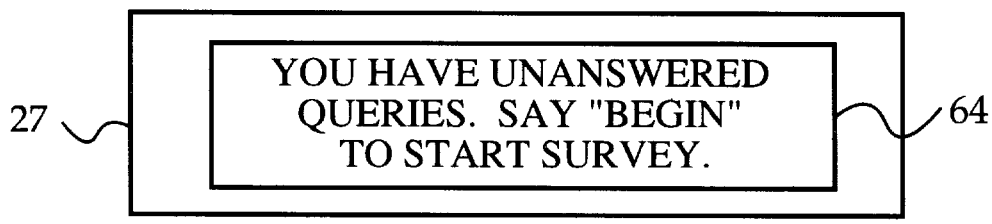
FIG. 14 is a sample prompt appearing on a display of the apparatus of FIG. 13.
Figure 15:
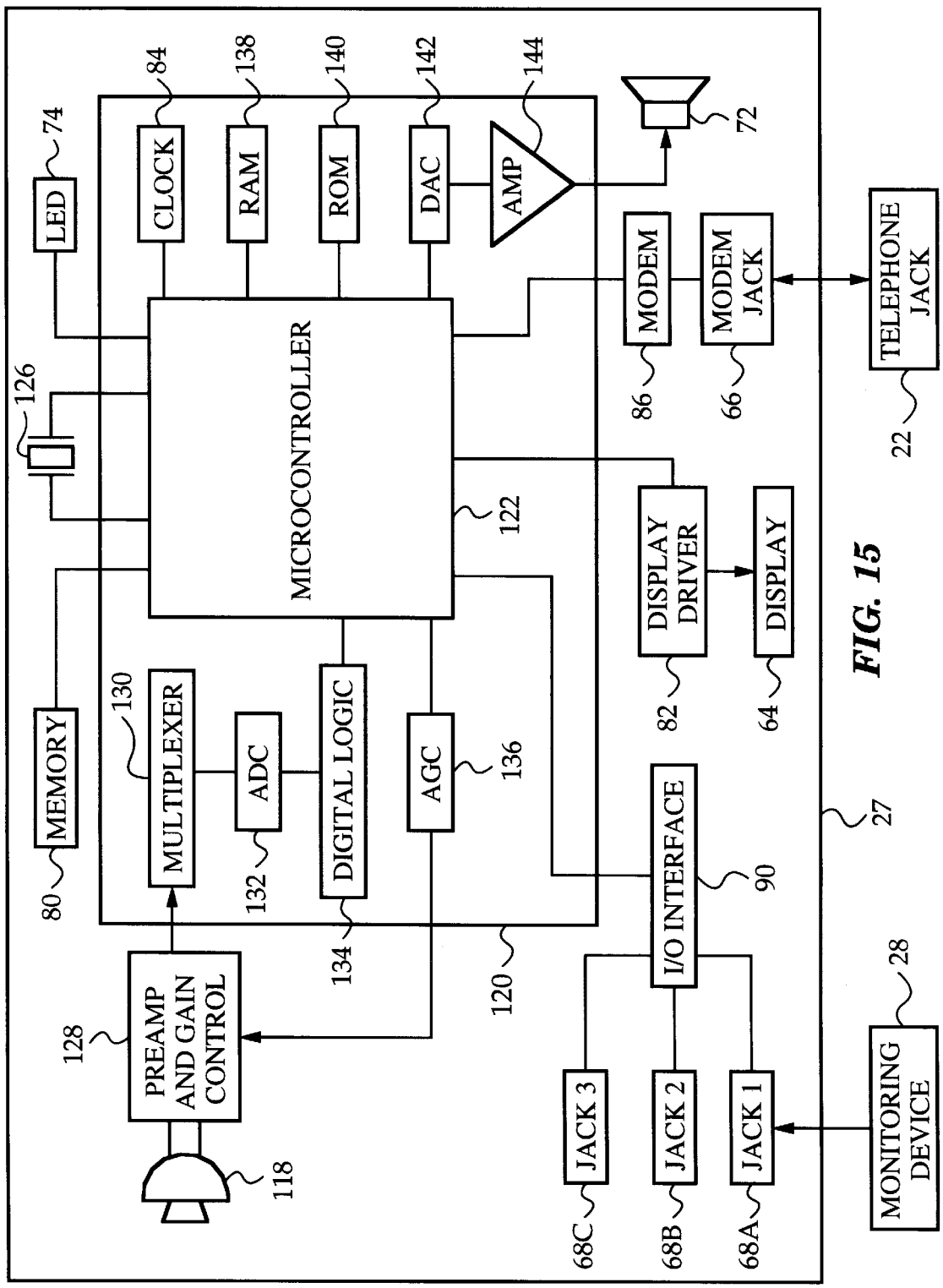
FIG. 15 is a block diagram illustrating the components of the apparatus of FIG. 13.

FIGS. 13–15 illustrate a second embodiment of the invention in which each remotely programmable apparatus has speech recognition and speech synthesis functionality. FIG. 13 shows a perspective view of remotely programmable apparatus 27 according to the second embodiment. Apparatus 27 includes a speaker 72 for audibly communicating queries and prompts to the patient. Apparatus 27 also includes a microphone 118 for receiving spoken responses to the queries and prompts. Apparatus 27 may optionally include a display 64 for displaying prompts to the patient, as shown in FIG. 14.

FIG. 15 is a schematic block diagram illustrating the components of apparatus 27 in greater detail. Apparatus 27 is similar in design to apparatus 26 of the preferred embodiment except that apparatus 27 includes an audio processor chip 120 in place of microprocessor 76. Audio processor chip 120 is preferably an RSC-164 chip commercially available from Sensory Circuits Inc. of 1735 N. First Street, San Jose, Calif. 95112.

Audio processor chip 120 has a microcontroller 122 for executing script programs received from server 18. A memory 80 is connected to microcontroller 122. Memory 80 stores the script programs and a script interpreter used by microcontroller 122 to execute the script programs. Memory 80 also stores measurements received from monitoring device 28, responses to the queries, script identification codes, and the patient's unique identification code.

Audio processor chip 120 also has built in speech synthesis functionality for synthesizing queries and prompts to a patient through speaker 72. For speech synthesis, chip 120 includes a digital to analog converter (DAC) 142 and an amplifier 144. DAC 142 and amplifier 144 drive speaker 72 under the control of microcontroller 122.

Audio processor chip 120 further has built in speech recognition functionality for recognizing responses spoken into microphone 118. Audio signals received through microphone 118 are converted to electrical signals and sent to a preamp and gain control circuit 128. Preamp and gain control circuit 128 is controlled by an automatic gain control circuit 136, which is in turn controlled by microcontroller 122. After being amplified by preamp 128, the electrical signals enter chip 120 and pass through a multiplexer 130 and an analog to digital converter (ADC) 132. The resulting digital signals pass through a digital logic circuit 134 and enter microcontroller 122 for speech recognition.

Audio processor chip 120 also includes a RAM 138 for short term memory storage and a ROM 140 which stores programs executed by microcontroller 122 to perform speech recognition and speech synthesis. Chip 120 operates at a clock speed determined by a crystal 126. Chip 120 also includes a clock 84 which provides the current date and time to microcontroller 122. As in the preferred embodiment, apparatus 27 includes an LED 74, display driver 82, modem 86, and device interface 90, all of which are connected to microcontroller 122.

The operation of the second embodiment is similar to the operation of the preferred embodiment except that queries, response choices, and prompts are audibly communicated to the patient through speaker 72 rather than being displayed to the patient on display 64. The operation of the second embodiment also differs from the operation of the preferred embodiment in that responses to the queries and prompts are received through microphone 118 rather than through user input buttons.

The script programs of the second embodiment are similar to the script program shown in FIGS. 6A–6B, except that each display command is replaced by a speech synthesis command and each input command is replaced by a speech recognition command. The speech synthesis commands are executed by microcontroller 122 to synthesize the queries, response choices, and prompts through speaker 72. The speech recognition commands are executed by microcontroller 122 to recognize responses spoken into microphone 118.

For example, to ask the patient how he or she feels and record a response, microcontroller 122 first executes a speech synthesis command to synthesize through speaker 72 "How do you feel? Please answer with one of the following responses: very bad, bad, good, or very good." Next, microcontroller 118 executes a speech recognition command to recognize the response spoken into microphone 118. The recognized response is stored in memory 80 and subsequently transmitted to the server. Other than the differences described, the operation and advantages of the second embodiment are the same as the operation and advantages of the preferred embodiment described above.

Although the first and second embodiments focus on querying individuals and collecting responses to the queries, the system of the invention is not limited to querying applications. The system may also be used simply to communicate messages to the individuals. FIGS. 16–19 illustrate a third embodiment in which the system is used to perform this automated messaging function. In the third embodiment, each script program contains a set of statements to be communicated to an individual rather than a set of queries to be answered by the individual. Of course, it will be apparent to one skilled in the art that the script programs may optionally include both queries and statements.

Figure 16:
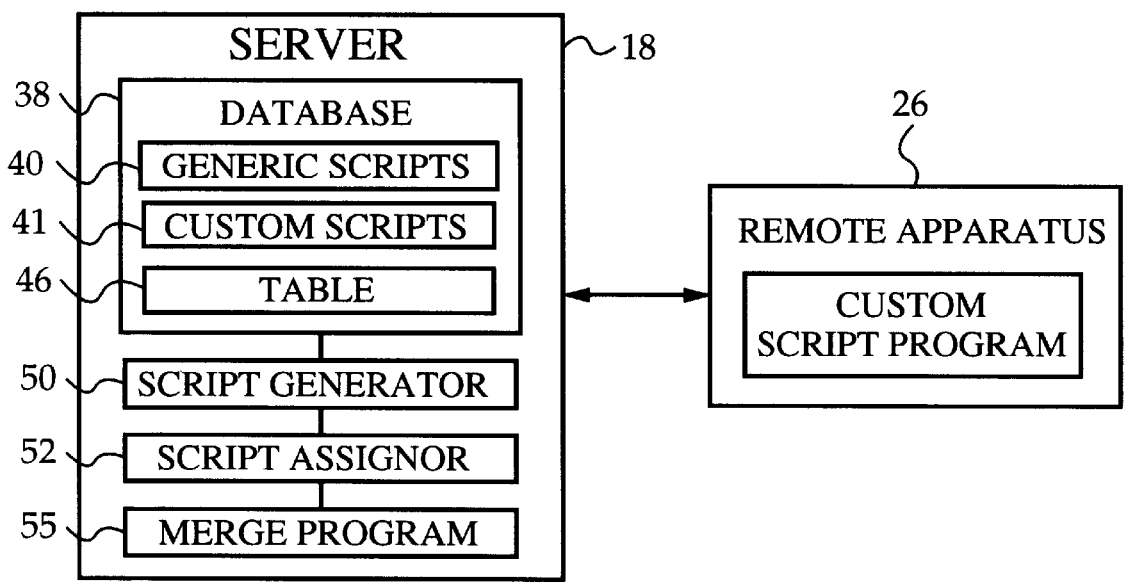
FIG. 16 is a schematic block diagram illustrating the interaction of the server of FIG. 1 with the apparatus of FIG. 3 according to a third embodiment of the invention.

The third embodiment also shows how the queries and statements may be customized to each individual by merging personal data with the script programs, much like a standard mail merge application. Referring to FIG. 16, personal data relating to each individual is preferably stored in look-up table 46 of database 38. By way of example, the data may include each individual's name, the name of each individual's physician, test results, appointment dates, or any other desired data. As in the preferred embodiment, database 38 also stores generic script programs 40 created by script generator 50.

Figure 17:
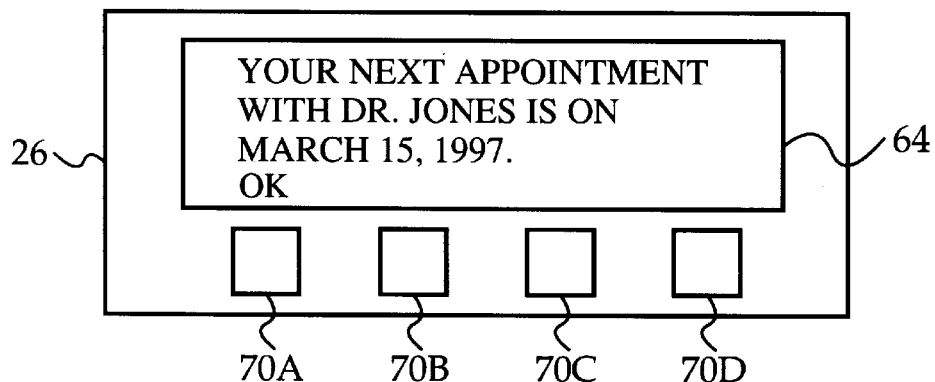
FIG. 17 is a first sample message appearing on the display of the apparatus of FIG. 3.
Figure 18:
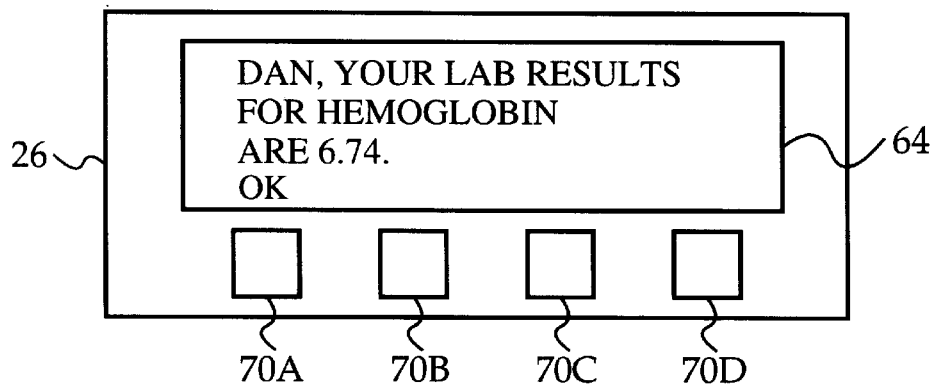
FIG. 18 is a second sample message appearing on the display of the apparatus of FIG. 3.

Server 18 includes a data merge program 55 for merging the data stored in table 46 with generic script programs 40. Data merge program 55 is designed to retrieve selected data from table 46 and to insert the data into statements in generic script programs 40, thus creating custom script programs 41. Each custom script program 41 contains statements which are customized to an individual. For example, the statements may be customized with the individual's name, test results, etc. Examples of such customized statements are shown in FIGS. 17–18.

Figure 19:
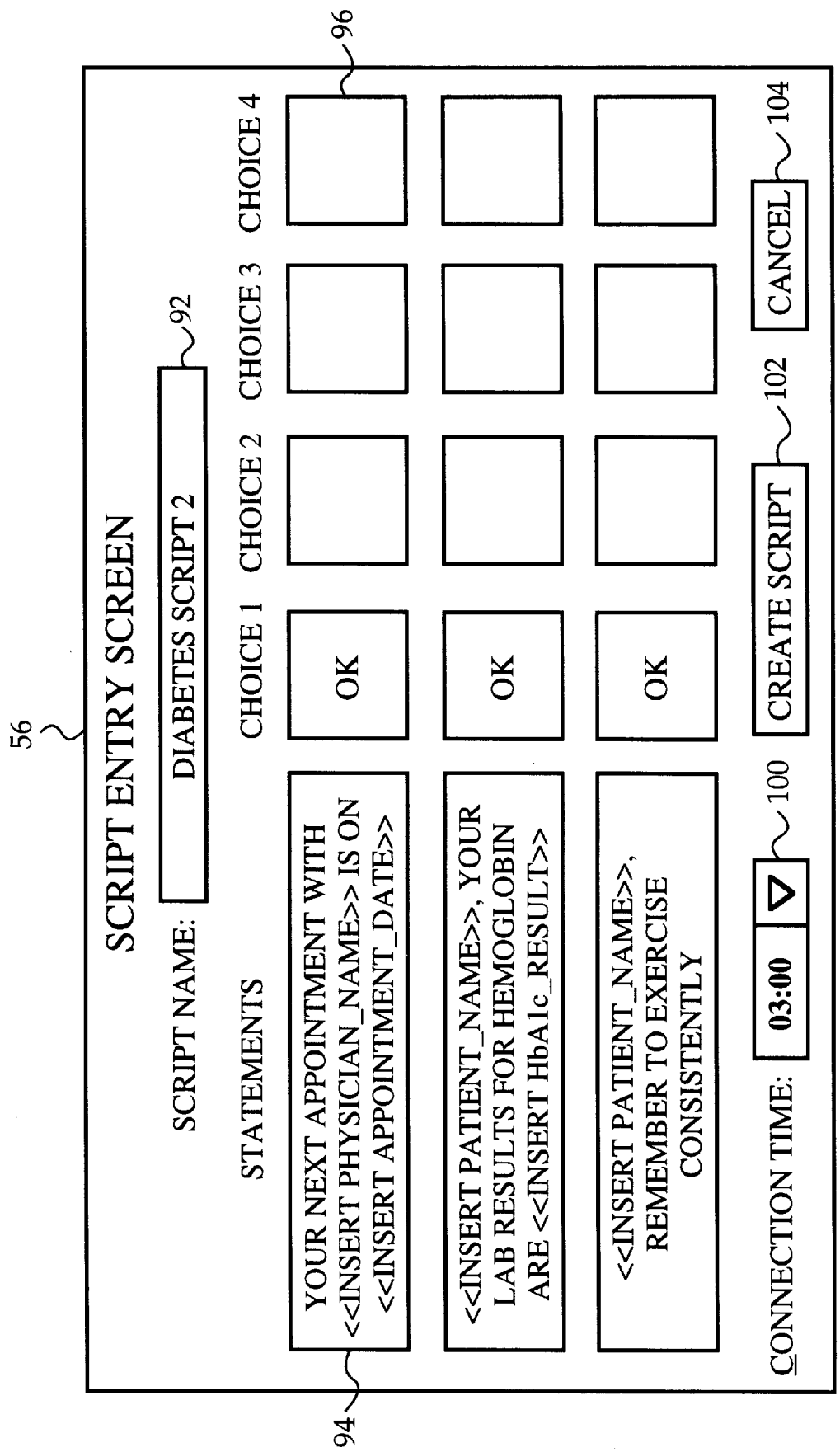
FIG. 19 is a script entry screen according to the third embodiment of the invention.

The operation of the third embodiment is similar to the operation of the preferred embodiment except that the script programs are used to communicate messages to the individuals rather than to query the individuals. Each message is preferably a set of statements. Referring to FIG. 19, the statements may be entered in server 18 through script entry screen 56, just like the queries of the preferred embodiment.

Each statement preferably includes one or more insert commands specifying data from table 46 to be inserted into the statement. The insert commands instruct data merge program 55 to retrieve the specified data from database 38 and to insert the data into the statement. For example, the insert commands shown in FIG. 19 instruct data merge program 55 to insert a physician name, an appointment date, a patient name, and a test result into the statements. As in the preferred embodiment, each statement may also include one or more response choices which are entered in fields 96.

Following entry of the statements and response choices, CREATE SCRIPT button 102 is pressed. When button 102 is pressed, script generator 50 generates a generic script program from the information entered in screen 56. The generic script program is similar to the script program shown in FIGS. 6A–6B, except that the display commands specify statements to be displayed rather than queries. Further, the statements include insert commands specifying data to be inserted into the script program. As in the preferred embodiment, multiple script programs are preferably generated, e.g. a generic script program for diabetes patients, a generic script program for asthma patients, etc. The generic script programs are stored in database 38.

Following generation of the generic script programs, server 18 receives script assignment information entered through script assignment screen 57. As shown in FIG. 7, the script programs are assigned by first selecting one of the generic script programs through check boxes 106, selecting individuals through check boxes 108, and pressing the ASSIGN SCRIPT button 112. When button 112 is pressed, data merge program 55 creates a custom script program 41 for each individual selected in check boxes 108.

Each custom script program 41 is preferably created by using the selected generic script program as a template. For each individual selected, data merge program 55 retrieves from database 38 the data specified in the insert commands. Next, data merge program 55 inserts the data into the appropriate statements in the generic script program 40 to create a custom script program 41 for the individual. Each custom script program 41 is stored in database 38.

As each custom script program 41 is generated for an individual, script assignor 52 assigns script program 41 to the individual. This is preferably accomplished by creating a pointer to the custom script program and storing the pointer with the individual's unique identification code in table 46. When the individual's remotely programmable apparatus connects to server 18, server 18 receives from remotely programmable apparatus 26 the individual's unique identification code. Server 18 uses the unique identification code to retrieve from table 46 the pointer to the custom script program assigned to the individual. Next, server 18 retrieves the assigned script program from database 38 and transmits the script program to the individual's remotely programmable apparatus 26 through communication network 24.

The apparatus receives and executes the script program. The execution of the script program is similar to the execution described in the preferred embodiment, except that statements are displayed to the individual rather than queries. FIGS. 17–18 illustrate two sample statements as they appear on display 64. Each statement includes a response choice, preferably an acknowledgment such as "OK". After reading a statement, the individual presses the button 70A–D corresponding to the response choice to proceed to the next statement. Alternatively, the script program may specify a period of time that each statement is to be displayed before proceeding to the next statement. The remaining operation of the third embodiment is analogous to the operation of the preferred embodiment described above.

Although it is presently preferred to generate a custom script program 41 for each individual as soon as script assignment information is received for the individual, it is also possible to wait until the individual's apparatus 26 connects to server 18 before generating custom script program 41. This is accomplished by creating and storing a pointer to the generic script program 40 assigned to the individual, as previously described in the preferred embodiment. When the individual's apparatus 26 connects to server 18, data merge program 55 creates a custom script program 41 for the individual from the generic script program 40 assigned to the individual. The custom script program 41 is then sent to the individual's apparatus 26 for execution.

SUMMARY, RAMIFICATIONS, AND SCOPE

Although the above description contains many specificities, these should not be construed as limitations on the scope of the invention but merely as illustrations of some of the presently preferred embodiments. Many other embodiments of the invention are possible. For example, the scripting language and script commands shown are representative of the preferred embodiment. It will be apparent to one skilled in the art many other scripting languages and specific script commands may be used to implement the invention.

Moreover, the invention is not limited to the specific applications described. The system and method of the invention have many other application both inside and outside the healthcare industry. For example, pharmaceutical manufacturers may apply the system in the clinical development and post marketing surveillance of new drugs, using the system as an interactive, on-line monitoring tool for collecting data on the efficacy, side effects, and quality of life impact of the drugs. Compared to the current use of labor intensive patient interviews, the system provides a fast, flexible, and cost effective alternative for monitoring the use and effects of the drugs.

The system may also be used by home healthcare companies to enhance the service levels provided to customers, e.g. panic systems, sleep surveillance, specific monitoring of disease conditions, etc. Alternatively, the system may be used to monitor and optimize the inventory of home stationed health supplies. As an example, the system may be connected to an appropriate measuring device to optimize timing of oxygen tank delivery to patients with chronic obstructive pulmonary disease (COPD).

The system and method of the invention also have many applications outside the healthcare industry. For example, the system may be used for remote education over the Internet, facilitating educational communication with children or adult trainees who lack access to sophisticated and expensive computer equipment. The system may also be used by law enforcement officers to perform on-line surveillance of individuals on probation or parole.

Further, the invention has numerous applications for gathering data from remotely located devices. For example, the system may be used to collect data from smart appliances, such as identification check systems. Alternatively, the system may be applied to the remote monitoring of facilities, including safety and security monitoring, or to environmental monitoring, including pollution control and pipeline monitoring. Many other suitable applications of the invention will be apparent to one skilled in the art.

Therefore, the scope of the invention should be determined not by the examples given, but by the appended claims and their legal equivalents.

What is claimed is:

1. A system for remotely monitoring an individual, the system comprising:
   a) a server;
   b) remote interface means for entering in the server a set of queries to be answered by the individual; and
   c) a remotely programmable apparatus for interacting with the individual, the remotely programmable apparatus being in communication with the server via a communication network;
   wherein the server comprises:
      i) script generating means for generating a script program from the set of queries, the script program being executable by the remotely programmable apparatus to communicate the set of queries to the individual, to receive responses to the set of queries, and to transmit the responses from the remotely programmable apparatus to the server; and
      ii) database means connected to the script generating means, the database means for storing the script program and the responses to the set of queries;
   and wherein the remotely programmable apparatus comprises:
      i) communication means for receiving the script program from the server and for transmitting the responses to the server;
      ii) user interface means for communicating the set of queries to the individual and for receiving the responses to the set of queries;
      iii) memory means for storing the script program and the responses to the set of queries; and
      iv) processor means connected to the communication means, the user interface means, and the memory means for executing the script program to communicate the set of queries to the individual, to receive the responses to the set of queries, and to transmit the responses to the server.

2. The system of claim 1, wherein the server comprises a web server having a web page for entry of the set of queries, and wherein the remote interface means is connected to the web server via the Internet.

3. The system of claim 1, wherein the user interface means comprises a display for displaying the queries, and user input buttons for entering the responses.

4. The system of claim 1, wherein the user interface means includes a speech synthesis means for audibly communicating the set of queries to the individual.

5. The system of claim 1, wherein the user interface means includes a speech recognition means for receiving spoken responses to the set of queries.

6. The system of claim 1, further comprising at least one monitoring device for producing measurements of a physiological condition of the individual and for transmitting the measurements to the remotely programmable apparatus, wherein the remotely programmable apparatus further includes device interface means connected to the processor means for receiving the measurements from the monitoring device, the memory means includes means for storing the measurements, and the communication means includes means for transmitting the measurements to the server.

7. The system of claim 6, wherein the device interface means includes means for interfacing with a plurality of monitoring devices, and the script program specifies a selected one of the plurality of monitoring devices from which to collect the measurements.

8. The system of claim 6, wherein the server further comprises report means for displaying the responses and the measurements on the remote interface means.

9. The system of claim 1, wherein the communication means includes means for establishing a first communication link to the server to receive the script program and means for establishing a subsequent communication link to the server to transmit the responses, and wherein the script program specifies a connection time at which to establish the subsequent communication link.

10. The system of claim 1, wherein the remotely programmable apparatus further comprises notification means connected to the processor means, the notification means for notifying the individual that unanswered queries are stored in the remotely programmable apparatus.

11. The system of claim 10, wherein the notification means comprises a visual indicator for visually notifying the individual.

12. The system of claim 10, wherein the notification means comprises a display for displaying a prompt.

13. The system of claim 1, further comprising a plurality of remotely programmable apparatuses in communication with the server, the plurality of remotely programmable apparatuses for remotely monitoring a corresponding plurality of individuals, wherein the database means includes means for storing a plurality of script programs, the remote interface means includes means for entering script assignment information, the server includes script assignment means connected to the database means for assigning to each of the plurality of individuals at least one of the plurality of script programs in accordance with the script assignment information, and the database means further includes means for storing a list of the plurality of individuals, and for each of the plurality of individuals, a respective pointer to the at least one of the plurality of script programs assigned to each of the plurality of individuals.

14. A method for remotely monitoring an individual, the method comprising the following steps:
   a) providing the individual with an apparatus having:
      i) a communication means for exchanging data with a server through a communication network, wherein the data includes a script program executable by the apparatus to communicate queries to the individual, to receive responses to the queries, and to transmit the responses to the server;
      ii) a memory means for storing the script program and the responses to the queries;
      iii) a user interface means for communicating the queries to the individual and for receiving the responses to the queries; and
      iv) a processor means connected to the communication means, the user interface means, and the memory means for executing the script program;
   b) entering in the server the queries to be answered by the individual;
   c) generating the script program from the queries;
   d) transmitting the script program from the server to the apparatus through the communication network;
   e) executing the script program in the apparatus to communicate the queries, to receive the responses, and to transmit the responses to the server; and
   f) receiving and storing the responses in the server.

15. The method of claim 14, wherein the server comprises a web server having a web page for entry of the queries, and wherein the queries are entered by accessing the web page through the Internet and entering the queries in the web page.

16. The method of claim 14, wherein the apparatus further comprises a device interface connected to the processor means for receiving from a monitoring device measurements of a physiological condition of the individual, and wherein the method further comprises the steps of:
   a) collecting the measurements in the apparatus through the device interface;
   b) transmitting the measurements from the apparatus to the server; and
   c) receiving and storing the measurements in the server.

17. The method of claim 16, wherein the device interface includes means for interfacing with a plurality of monitoring devices, the script program specifies a selected one of the plurality of monitoring devices from which to collect the measurements, and the method further comprises the step of prompting the individual to connect the selected one of the plurality of monitoring devices to the device interface.

18. The method of claim 16, further comprising the step of reporting on a remote interface the responses and measurements received in the server.

19. The method of claim 14, wherein the script program is transmitted from the server to the apparatus through a first communication link, the responses to the queries are transmitted from the apparatus to the server through a subsequent communication link, and the script program specifies a connection time at which to establish the subsequent communication link.

20. The method of claim 14, further comprising the step of notifying the individual when unanswered queries are stored in the apparatus.

21. The method of claim 20, wherein the apparatus further comprises a visual indicator connected to the processor means and the step of notifying the individual comprises lighting the visual indicator.

22. The method of claim 20, wherein the apparatus further comprises a display connected to the processor means and the step of notifying the individual comprises displaying a prompt on the display.

23. The method of claim 14, wherein the user interface means comprises a display and input buttons, and wherein the queries are communicated through the display and the responses are received through the input buttons.

24. The method of claim 14, wherein the user interface means includes a speech synthesizer, and wherein the queries are communicated through the speech synthesizer.

25. The method of claim 14, wherein the user interface means includes a speech recognizer, and wherein the responses are received through the speech recognizer.

26. The method of claim 14, further comprising the steps of:
   a) providing a plurality of individuals with a corresponding plurality of apparatuses such that each of the plurality of individuals is associated with a respective one of the plurality of apparatuses;
   b) entering in the server a plurality of sets of queries;
   c) generating in the server a plurality of script programs such that each of the plurality of script programs corresponds to a respective one of the plurality of sets of queries;
   d) assigning to each of the plurality of individuals at least one of the plurality of script programs;
   e) storing in the server the plurality of script programs, a list of the plurality of individuals, and for each of the plurality of individuals, a respective pointer to the at least one of the plurality of script programs assigned to each of the plurality of individuals; and
   f) transmitting to each of the plurality of apparatuses the at least one of the plurality of script programs assigned to each of the plurality of individuals associated with the respective one of the plurality of apparatuses.

27. The system of claim 1, wherein the communication means comprises a modem.

28. The system of claim 1, wherein the system is adapted to allow the individual to select a time at which to respond to the set of queries.

29. The system of claim 1, wherein the server includes a merge program and a database, said database including a look-up table, said look-up table for storing personal data relating to the individual, and said merge program for merging the personal data with at least one generic script program to provide at least one custom script program.

30. The system of claim 29, wherein the at least one custom script program contains information customized to the individual.

31. A system for communicating information to an individual, the system comprising:
   a) a server;
   b) a remote interface means connected to the server, the remote interface means for specifying a message to be communicated to the individual; and
   c) a remotely programmable apparatus for communicating the message to the individual, the remotely programmable apparatus being networked to the server via a communication network;

wherein the server includes a script generating means for generating a script program executable by the remotely programmable apparatus to communicate the message to the individual;

and wherein the apparatus comprises:
- i) communication means for receiving the script program from the server;
- ii) memory means for storing the script program;
- iii) user interface means for communicating the message to the individual; and
- iv) processor means connected to the communication means, the user interface means, and the memory means for executing the script program.

32. The system of claim 31, wherein the server further includes database means connected to the script generating means, the database means for storing data relating to the individual, and wherein the script generating means includes means for inserting the data into the script program to customize the message to the individual.

33. The system of claim 31, wherein the server comprises a web server, and wherein the remote interface means is connected to the web server via the Internet.

34. The system of claim 31, wherein the user interface means comprises a display for displaying the message to the individual.

35. The system of claim 31, wherein the user interface means comprises a speech synthesis means for audibly communicating the message to the individual.

36. The system of claim 31, wherein the communication means includes means for establishing a first communication link to the server to receive a first script program and means for establishing a subsequent communication link to the server to receive a new script program, and wherein the first script program specifies a connection time at which to establish the subsequent communication link.

37. The system of claim 31, wherein the remotely programmable apparatus further includes notification means, the notification means connected to the processor means for notifying the individual that a new message has been received.

38. The system of claim 37, wherein the notification means comprises a visual indicator for visually notifying the individual.

39. The system of claim 37, wherein the notification means comprises a display for displaying a prompt.

40. The system of claim 31, further comprising a plurality of remotely programmable apparatuses networked to the server for communicating information to a corresponding plurality of individuals, wherein the server includes database means for storing a plurality of script programs, the remote interface means includes means for entering in the server script assignment information, the server includes script assignment means connected to the database means for assigning to each of the plurality of individuals at least one of the plurality of script programs in accordance with the script assignment information, and the database means further includes means for storing a list of the plurality of individuals, and for each of the plurality of individuals, a respective pointer to the at least one of the plurality of script programs assigned to each of the plurality of individuals.

41. A method for communicating information to an individual, the method comprising the following steps:
- a) providing the individual with an apparatus having:
    - i) a communication means for exchanging data with a server through a communication network, wherein the data includes a script program executable by the apparatus to communicate a message to the individual;
    - ii) a memory means for storing the script program;
    - iii) a user interface for communicating the message; and
    - iv) a processor means connected to the communication means, the memory means, and the user interface for executing the script program;
- b) entering in the server the message to be communicated to the individual;
- c) generating the script program in the server;
- d) transmitting the script program from the server to the apparatus through the communication network; and
- e) executing the script program in the apparatus to communicate the message to the individual.

42. The method of claim 41, wherein the step of transmitting the script program from the server to the apparatus is preceded by the steps of: storing in the server data relating to the individual, and inserting the data into the script program to customize the message to the individual.

43. The method of claim 41, wherein the server comprises a web server having a web page for entry of the message, and wherein the message is entered in the server by accessing the web page through the Internet and entering the message in the web page.

44. The method of claim 41, wherein the script program is transmitted from the server to the apparatus through a first communication link, the script program specifies a connection time at which the apparatus is to establish a subsequent communication link to the server, and the method further comprises the steps of establishing the subsequent communication link at the specified connection time and receiving a new script program in the apparatus through the subsequent communication link.

45. The method of claim 41, further comprising the step of notifying the individual when a new message has been received in the apparatus.

46. The method of claim 45, wherein the apparatus further comprises a visual indicator connected to the processor means and the step of notifying the individual comprises lighting the visual indicator.

47. The method of claim 45, wherein the apparatus further comprises a display connected to the processor means and the step of notifying the individual comprises displaying a prompt on the display.

48. The method of claim 41, wherein the user interface comprises a display, and the message is communicated to the individual by displaying the message on the display.

49. The method of claim 41, wherein the user interface comprises a speech synthesizer, and the message is communicated to the individual by audibly synthesizing the message through the speech synthesizer.

50. The method of claim 41, further comprising the steps of:
- a) providing a plurality of individuals with a corresponding plurality of apparatuses such that each of the plurality of individuals is associated with a respective one of the plurality of apparatuses;
- b) generating in the server a plurality of script programs;
- c) assigning to each of the plurality of individuals at least one of the plurality of script programs;
- d) storing in the server the plurality of script programs, a list of the plurality of individuals, and for each of the plurality of individuals, a respective pointer to the at least one of the plurality of script programs assigned to each of the plurality of individuals; and
- e) transmitting to each of the plurality of apparatuses the at least one of the plurality of script programs assigned to each of the plurality of individuals associated with the respective one of the plurality of apparatuses.

* * * * *

US005997476C1

(12) EX PARTE REEXAMINATION CERTIFICATE (10020th)
United States Patent
Brown

(10) Number: US 5,997,476 C1
(45) Certificate Issued: Jan. 30, 2014

(54) NETWORKED SYSTEM FOR INTERACTIVE COMMUNICATION AND REMOTE MONITORING OF INDIVIDUALS

(75) Inventor: Stephen J. Brown, Mountain View, CA (US)

(73) Assignee: Health Hero Network, Mountain View, CA (US)

Reexamination Request:
No. 90/012,768, Jan. 21, 2013

Reexamination Certificate for:
Patent No.: 5,997,476
Issued: Dec. 7, 1999
Appl. No.: 08/946,341
Filed: Oct. 7, 1997

Related U.S. Application Data

(63) Continuation-in-part of application No. 08/847,009, filed on Apr. 30, 1997, now Pat. No. 5,897,493.

(60) Provisional application No. 60/041,746, filed on Mar. 28, 1997, provisional application No. 60/041,751, filed on Mar. 28, 1997.

(51) Int. Cl.
*A61N 5/00* (2006.01)

(52) U.S. Cl.
USPC .............. 600/300; 600/301; 128/920; 705/2; 705/3

(58) Field of Classification Search
None
See application file for complete search history.

(56) References Cited

To view the complete listing of prior art documents cited during the proceeding for Reexamination Control Number 90/012,768, please refer to the USPTO's public Patent Application Information Retrieval (PAIR) system under the Display References tab.

*Primary Examiner* — Joshua Campbell

(57) ABSTRACT

The invention presents a networked system for communicating information to an individual and for remotely monitoring the individual. The system includes a server and a remote interface for entering in the server a set of queries to be answered by the individual. The server is preferably a web server and the remote interface is preferably a personal computer or remote terminal connected to the server via the Internet. The system also includes a remotely programmable apparatus connected to the server via a communication network, preferably the Internet. The apparatus interacts with the individual in accordance with a script program received from the server. The server includes a script generator for generating the script program from the set of queries entered through the remote interface. The script program is received and executed by the apparatus to communicate the queries to the individual, to receive responses to the queries, and to transmit the responses from the apparatus to the server.

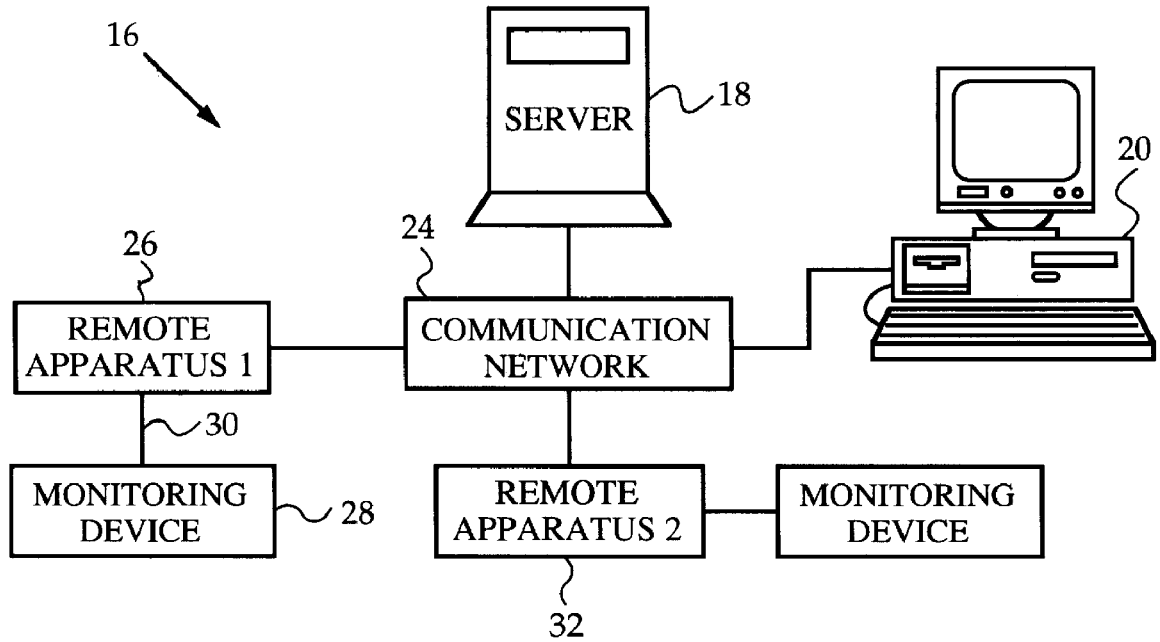

US 5,997,476 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2, 13, 15, 26, 29, 30, 36, 40, 43, 44 and 50 is confirmed.

Claims 1, 14, 31 and 41 are cancelled.

Claims 3-6, 9, 10, 16, 19, 20, 23-25, 27, 28, 32-35, 37, 42, 45, 48 and 49 are determined to be patentable as amended.

Claims 7, 8, 11, 12, 17, 18, 21, 22, 38, 39, 46 and 47, dependent on an amended claim, are determined to be patentable.

New claims 51-87 are added and determined to be patentable.

3. The system of claim [1] *2*, wherein the user interface means comprises a display for displaying the queries, and user input buttons for entering the responses.

4. The system of claim [1] *2*, wherein the user interface means includes a speech synthesis means for audibly communicating the set of queries to the individual.

5. The system of claim [1] *2*, wherein the user interface means includes a speech recognition means for receiving spoken responses to the set of queries.

6. The system of claim [1] *2*, further comprising at least one monitoring device for producing measurements of a physiological condition of the individual and for transmitting the measurements to the remotely programmable apparatus, wherein the remotely programmable apparatus further includes device interface means connected to the processor means for receiving the measurements from the monitoring device, the memory means includes means for storing the measurements, and the communication means includes means for transmitting the measurements to the server.

9. The system of claim [1] *2*, wherein the communication means includes means for establishing a first communication link to the server to receive the script program and means for establishing a subsequent communication link to the server to transmit the responses, and wherein the script program specifies a connection time at which to establish the subsequent communication link.

10. The system of claim [1] *2*, wherein the remotely programmable apparatus further comprises notification means connected to the processor means, the notification means for notifying the individual that unanswered queries are stored in the remotely programmable apparatus.

16. The method of claim [14] *15*, wherein the apparatus further comprises a device interface connected to the processor means for receiving from a monitoring device measurements of a physiological condition of the individual, and wherein the method further comprises the steps of:
 a) collecting the measurements in the apparatus through the device interface;
 b) transmitting the measurements from the apparatus to the server; and
 c) receiving and storing the measurements in the server.

19. The method of claim [14] *15*, wherein the script program is transmitted from the server to the apparatus through a first communication link, the responses to the queries are transmitted from the apparatus to the server through a subsequent communication link, and the script program specifies a connection time at which to establish the subsequent communication link.

20. The method of claim [14] *15*, further comprising the step of notifying the individual when unanswered queries are stored in the apparatus.

23. The method of claim [14] *15*, wherein the user interface means comprises a display and input buttons, and wherein the queries are communicated through the display and the responses are received through the input buttons.

24. The method of claim [14] *15*, wherein the user interface means includes a speech synthesizer, and wherein the queries are communicated through the speech synthesizer.

25. The method of claim [14] *15*, wherein the user interface means includes a speech recognizer, and wherein the responses are received through the speech recognizer.

27. The system of claim [1] *2*, wherein the communication means comprises a modem.

28. The system of claim [1] *2*, wherein the system is adapted to allow the individual to select a time at which to respond to the set of queries.

32. The system of claim [31] *36*, wherein the server further includes database means connected to the script generating means, the database means for storing data relating to the individual, and wherein the script generating means includes means for inserting the data into the script program to customize the message to the individual.

33. The system of claim [31] *36*, wherein the server comprises a web server, and wherein the remote interface means is connected to the web server via the Internet.

34. The system of claim [31] *36*, wherein the user interface means comprises a display for displaying the message to the individual.

35. The system of claim [31]*36*, wherein the user interface means comprises a speech synthesis means for audibly communicating the message to the individual.

37. The system of claim [31] *36*, wherein the remotely programmable apparatus further includes notification means, the notification means connected to the processor means for notifying the individual that a new message has been received.

42. The method of claim [41] *43*, wherein the step of transmitting the script program from the server to the apparatus is preceded by the steps of: storing in the server data relating to the individual, and inserting the data into the script program to customize the message to the individual.

45. The method of claim [41] *43*, further comprising the step of notifying the individual when a new message has been received in the apparatus.

48. The method of claim [41] *43*, wherein the user interface comprises a display, and the message is communicated to the individual by displaying the message on the display.

49. The method of claim [41] *43*, wherein the user interface comprises a speech synthesizer, and the message is communicated to the individual by audibly synthesizing the message through the speech synthesizer.

*51. The system of claim 13, wherein the user interface means comprises a display for displaying the queries, and user input buttons for entering the responses.*

52. The system of claim 13, wherein the user interface means includes a speech synthesis means for audibly communicating the set of queries to the individual.

53. The system of claim 13, wherein the user interface means includes a speech recognition means for receiving spoken responses to the set of queries.

54. The system of claim 13, further comprising at least one monitoring device for producing measurements of a physiological condition of the individual and for transmitting the measurements to the remotely programmable apparatus, wherein the remotely programmable apparatus further includes device interface means connected to the processor means for receiving the measurements from the monitoring device, the memory means includes means for storing the measurements, and the communication means includes means for transmitting the measurements to the server.

55. The system of claim 54, wherein the device interface means includes means for interfacing with a plurality of monitoring devices, and the script program specifies a selected one of the plurality of monitoring devices from which to collect the measurements.

56. The system of claim 54, wherein the server further comprises report means for displaying the responses and the measurements on the remote interface means.

57. The system of claim 13, wherein the communication means includes means for establishing a first communication link to the server to receive the script program and means for establishing a subsequent communication link to the server to transmit the responses, and wherein the script program specifies a connection time at which to establish the subsequent communication link.

58. The system of claim 13, wherein the remotely programmable apparatus further comprises notification means connected to the processor means, the notification means for notifying the individual that unanswered queries are stored in the remotely programmable apparatus.

59. The system of claim 13, wherein the communication means comprises a modem.

60. The system of claim 13, wherein the system is adapted to allow the individual to select a time at which to respond to the set of queries.

61. The system of claim 29, wherein the user interface means comprises a display for displaying the queries, and user input buttons for entering the responses.

62. The system of claim 29, wherein the user interface means includes a speech synthesis means for audibly communicating the set of queries to the individual.

63. The system of claim 29, wherein the user interface means includes a speech recognition means for receiving spoken responses to the set of queries.

64. The system of claim 29, further comprising at least one monitoring device for producing measurements of a physiological condition of the individual and for transmitting the measurements to the remotely programmable apparatus, wherein the remotely programmable apparatus further includes device interface means connected to the processor means for receiving the measurements from the monitoring device, the memory means includes means for storing the measurements, and the communication means includes means for transmitting the measurements to the server.

65. The system of claim 64, wherein the device interface means includes means for interfacing with a plurality of monitoring devices, and the script program specifies a selected one of the plurality of monitoring devices from which to collect the measurements.

66. The system of claim 64, wherein the server further comprises report means for displaying the responses and the measurements on the remote interface means.

67. The system of claim 29, wherein the communication means includes means for establishing a first communication link to the server to receive the script program and means for establishing a subsequent communication link to the server to transmit the responses, and wherein the script program specifies a connection time at which to establish the subsequent communication link.

68. The system of claim 29, wherein the remotely programmable apparatus further comprises notification means connected to the processor means, the notification means for notifying the individual that unanswered queries are stored in the remotely programmable apparatus.

69. The system of claim 29, wherein the communication means comprises a modem.

70. The system of claim 29, wherein the system is adapted to allow the individual to select a time at which to respond to the set of queries.

71. The method of claim 26, wherein the apparatus further comprises a device interface connected to the processor means for receiving from a monitoring device measurements of a physiological condition of the individual, and wherein the method further comprises the steps of:
 a) collecting the measurements in the apparatus through the device interface;
 b) transmitting the measurements from the apparatus to the server; and
 c) receiving and storing the measurements in the server.

72. The method of claim 71, wherein the device interface includes means for interfacing with a plurality of monitoring devices, the script program specifies a selected one of the plurality of monitoring devices from which to collect the measurements, and the method further comprises the step of prompting the individual to connect the selected one of the plurality of monitoring devices to the device interface.

73. The method of claim 71, further comprising the step of reporting on a remote interface the responses and measurements received in the server.

74. The method of claim 26, wherein the script program is transmitted from the server to the apparatus through a first communication link, the responses to the queries are transmitted from the apparatus to the server through a subsequent communication link, and the script program specifies a connection time at which to establish the subsequent communication link.

75. The method of claim 26, further comprising the step of notifying the individual when unanswered queries are stored in the apparatus.

76. The method of claim 75, wherein the apparatus further comprises a visual indicator connected to the processor means and the step of notifying the individual comprises lighting the visual indicator.

77. The method of claim 75, wherein the apparatus further comprises a display connected to the processor means and the step of notifying the individual comprises displaying a prompt on the display.

78. The method of claim 26, wherein the user interface means comprises a display and input buttons, and wherein the queries are communicated through the display and the responses are received through the input buttons.

79. The method of claim 26, wherein the user interface means includes a speech synthesizer, and wherein the queries are communicated through the speech synthesizer.

80. The method of claim 26, wherein the user interface means includes a speech recognizer, and wherein the responses are received through the speech recognizer.

81. The method of claim 44, wherein the step of transmitting the script program from the server to the apparatus is preceded by the steps of: storing in the server data relating to the individual, and inserting the data into the script program to customize the message to the individual.

82. The method of claim 44, wherein the server comprises a web server having a web page for entry of the message, and wherein the message is entered in the server by accessing the web page through the Internet and entering the message in the web page.

83. The method of claim 44, further comprising the step of notifying the individual when a new message has been received in the apparatus.

84. The method of claim 83, wherein the apparatus further comprises a visual indicator connected to the processor means and the step of notifying the individual comprises lighting the visual indicator.

85. The method of claim 83, wherein the apparatus further comprises a display connected to the processor means and the step of notifying the individual comprises displaying a prompt on the display.

86. The method of claim 44, wherein the user interface comprises a display, and the message is communicated to the individual by displaying the message on the display.

87. The method of claim 44, wherein the user interface comprises a speech synthesizer, and the message is communicated to the individual by audibly synthesizing the message through the speech synthesizer.

* * * * *